(12) United States Patent
Wang

(10) Patent No.: US 8,957,033 B2
(45) Date of Patent: Feb. 17, 2015

(54) INHIBITOR OF SODIUM-DEPENDENT GLUCOSE TRANSPORT PROTEIN AND PREPARATION METHOD THEREFOR AND USE THEREOF

(75) Inventor: Michael Wang, Beijing (CN)

(73) Assignee: Beijing Prelude Pharm. SCI. & Tech. Co., Ltd., Beijing (CN)

(*) Notice: Subject to any disclaimer, the term of this patent is extended or adjusted under 35 U.S.C. 154(b) by 0 days.

(21) Appl. No.: 14/114,197

(22) PCT Filed: Feb. 20, 2012

(86) PCT No.: PCT/CN2012/071375
§ 371 (c)(1),
(2), (4) Date: Oct. 25, 2013

(87) PCT Pub. No.: WO2012/146075
PCT Pub. Date: Nov. 1, 2012

(65) Prior Publication Data
US 2014/0051648 A1    Feb. 20, 2014

Related U.S. Application Data

(60) Provisional application No. 61/478,796, filed on Apr. 25, 2011.

(51) Int. Cl.
| | | |
|---|---|---|
| *A61K 31/70* | (2006.01) | |
| *C07H 1/00* | (2006.01) | |
| *C07H 5/02* | (2006.01) | |
| *C07D 309/10* | (2006.01) | |
| *A61K 9/00* | (2006.01) | |
| *A61K 9/16* | (2006.01) | |
| *A61K 9/20* | (2006.01) | |
| *A61K 31/351* | (2006.01) | |
| *A61K 45/06* | (2006.01) | |
| *C07H 7/04* | (2006.01) | |

(52) U.S. Cl.
CPC .............. *A61K 31/70* (2013.01); *C07D 309/10* (2013.01); *A61K 9/0019* (2013.01); *A61K 9/1623* (2013.01); *A61K 9/1635* (2013.01); *A61K 9/1652* (2013.01); *A61K 9/2018* (2013.01); *A61K 9/2027* (2013.01); *A61K 9/2059* (2013.01); *A61K 31/351* (2013.01); *A61K 45/06* (2013.01); *C07H 7/04* (2013.01)
USPC ............ 514/23; 536/1.11; 536/122; 536/124

(58) Field of Classification Search
None
See application file for complete search history.

(56) References Cited

U.S. PATENT DOCUMENTS

| | | | | |
|---|---|---|---|---|
| 7,683,160 | B2 * | 3/2010 | Eckhardt et al. | 536/1.11 |
| 7,687,469 | B2 * | 3/2010 | Eckhardt et al. | 514/23 |
| 7,838,499 | B2 * | 11/2010 | Chen et al. | 514/23 |

OTHER PUBLICATIONS

Adachi et al., Metabolism, vol. 49, No. 8, 2000, 990-995.*

* cited by examiner

*Primary Examiner* — Traviss C McIntosh, III
(74) *Attorney, Agent, or Firm* — Christie, Parker & Hale, LLP

(57) ABSTRACT

Disclosed is a compound of formula I, or a pharmaceutically acceptable salt, solvate, polymorph, enantiomer or racemic mixture thereof, wherein R1 and R2 are each independently hydrogen, —OH, alkyl, —$CF_3$, —$OCHF_2$, —$OCF_3$ or halogen; R3 is cycloalkyl, —$OCH_2CF_3$, —$OCH_2CHF_2$, —$OCH_2CH_2F$ or —$OCH_2CH_3$; R4 is hydrogen, —OH, —O aryl, —$OCH_2$ aryl, alkyl, cycloalkyl, —$CF_3$, —$OCHF_2$, —$OCF_3$, —$OCH_2CF_3$, —$OCH_2CHF_2$, —$OCH_2CH_2F$ or halogen; A is —$CX_1X_2$, wherein $X_1$ and $X_2$ are each independently H, F and Cl, and when both X1 and X2 are H, R3 is not —$OCH_2CH_3$. The compound has an activity of inhibitors of sodium-dependent glucose transport protein. Also disclosed is a method for preparing the compound, a pharmaceutical composition comprising the compound, use of the compound and pharmaceutical composition thereof in preparing medicaments of SGLT2 inhibitors and treating related diseases.

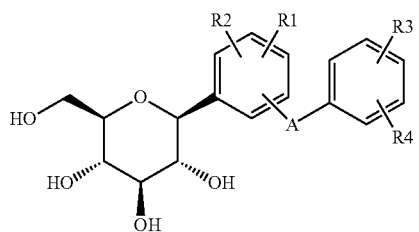

23 Claims, 5 Drawing Sheets

1A

1B

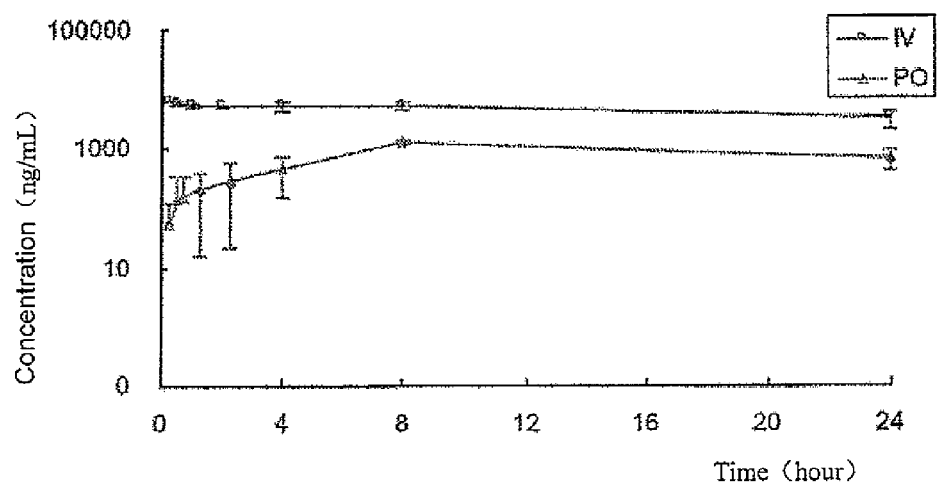
1C
Fig. 2
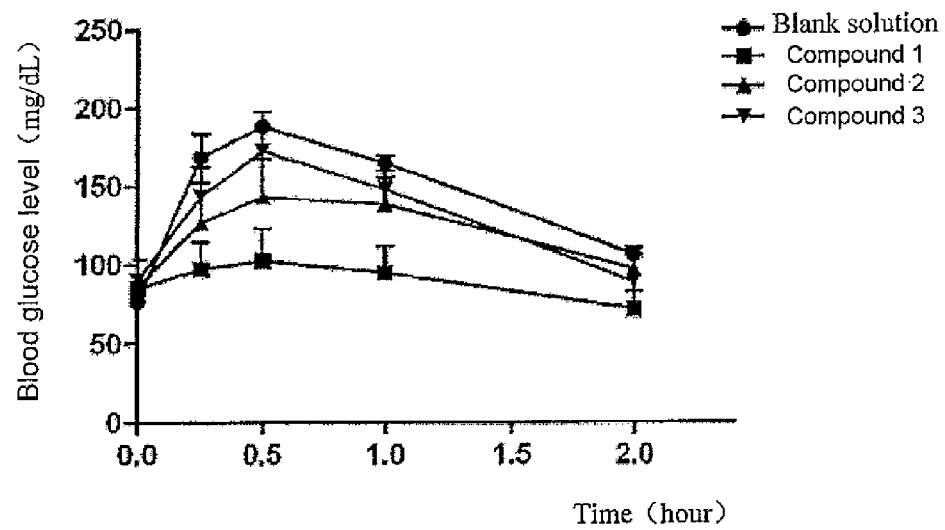
2A

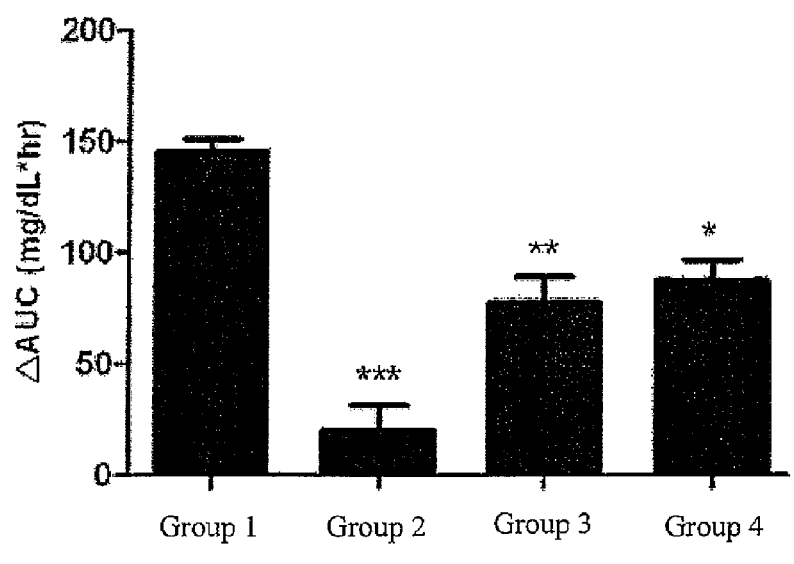
2B
Fig. 3
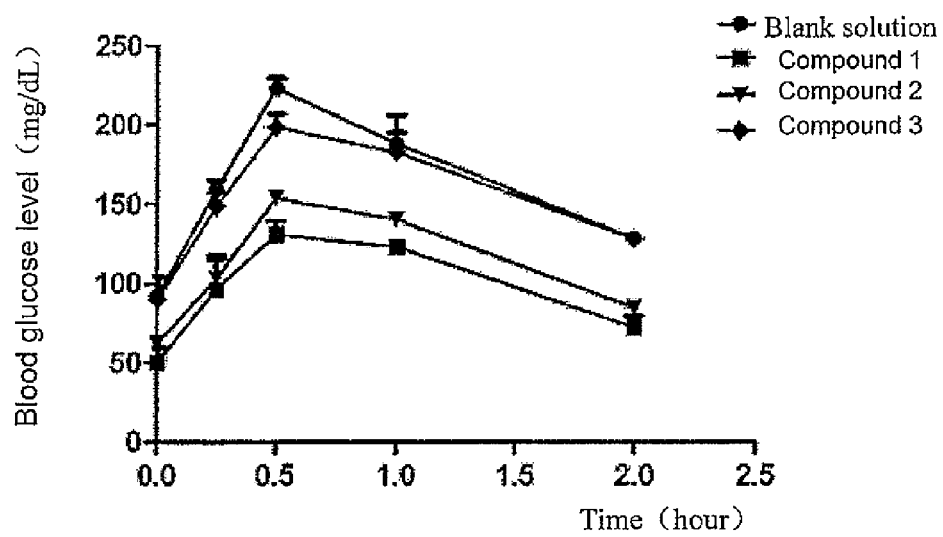

4A

4B

INHIBITOR OF SODIUM-DEPENDENT GLUCOSE TRANSPORT PROTEIN AND PREPARATION METHOD THEREFOR AND USE THEREOF

CROSS-REFERENCE TO RELATED APPLICATION

This application is a National Phase Patent Application and claims the priority of International Application Number PCT/CN2012/071375, filed on Feb. 20, 2012, which claims the benefit of U.S. Provisional Application No. 61/478,796, filed on Apr. 25, 2011.

TECHNICAL FIELD

The present invention belongs to the field of medicaments, specifically, the present invention relates to a novel compound having an activity of inhibitors of sodium-dependent glucose transport protein (SGLT2), a method for preparing the compound, pharmaceutical composition comprising the compound, and use of the compound and the pharmaceutical composition in preparing medicaments of SGLT2 inhibitors and treating related diseases.

BACKGROUND

Research data show that the number of patients with diabetes worldwide is increased to 280 million from 150 million in 2000, and is expected to reach approximately 500 million in 2030. Diabetes can lead to infection, heart disease, cerebrovascular disease, kidney failure, blindness of both eyes, lower limb gangrene, etc. causing huge impact and injury to the patient's physical and mental health and normal life.

Pathologically, diabetes is a series of clinical syndromes resulting from absolute or relative lack of insulin in vivo. World Health Organization (WHO) divides the diabetes into four types: type 1 diabetes, type 2 diabetes, secondary diabetes and gestational diabetes. All of different types of diabetes are incapable of making β cells in the pancreas produce enough insulin to lower the concentration of blood glucose, leading to the occurrence of hyperglycemia. Wherein type 2 diabetes (NIDDM), also known as non-insulin-dependent diabetes, often happens to adults, especially obese patients, accounting for over 90% of patients with diabetes, which is particularly serious. Patients with early type 2 diabetes can be controlled by improving lifestyle (such as adopting healthy diet, regular exercise, etc), most patients need to be administrated with hypoglycemic drugs orally or injected with insulin to help control blood glucose, but the therapeutic route and its therapeutic effect is limited.

Type 2 diabetes is characterized in hyperglycemia due to excessive hepatic glucose produced and peripheral insulin resistance. Hyperglycemia is considered to be a major risk factor for complications of diabetes, and may be directly related to impaired insulin secretion in advanced NIDDM. Therefore, it is generally believed that normalization of NIDDM patient's blood glucose will improve the action of insulin and offset the development of diabetic complications.

It is known that there is no sugar in urine under normal physiological conditions. This is because blood is filtrated through glomerulus and all of blood glucose filtrated enters into the crude urine and then reabsorbed after passing through renal proximal tubule. This reabsorption procedure is performed through sodium-glucose co-transport protein (SGLTs). SGLTs include SGLT1 and SGLT2, wherein SGLT1 is expressed in the small intestine and S3 segment at far end of the renal proximal tubule, and absorbs about 10% of the glucose; SGLT2 is mainly expressed in the front S1 segment of the renal proximal tubule and responsible for reabsorption of over 90% of the glucose. Thus inhibiting SGLTs, particularly SGLT2 can inhibit the reabsorption of glucose, such that glucose can be discharged in urine. Studies have shown that administering SGLT2 inhibitors to model animals with diabetes can improve the response of insulin to blood glucose, increase sensitivity of insulin, and delay the onset of nephropathy and neuropathy. Thus, for type 2 diabetic patients, the selective inhibition to SGLT2 may increase the excretion of glucose in urine, so as to normalize the plasma glucose, thereby increasing sensitivity of insulin and delaying the development of diabetic complications.

Thus, using selective inhibitors of SGLT2 as drugs will help to treat, improve or prevent the onset and development of diabetes and related diseases. Compounds for inhibiting SGLT2 have been proposed to be used as candidates of anti-diabetic drugs, and some C-aryl glucoside SGLT2 inhibitors have been developed, such as dapagliflozin represented by the following formula:

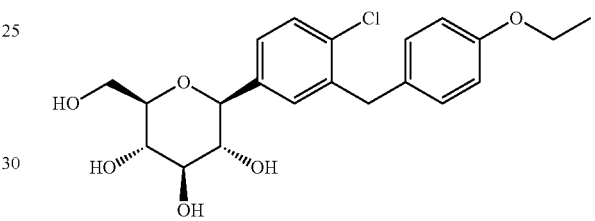

Dapagliflozin (referred to as "compound 1" in other parts of the present invention) is researched and developed by the Bristol-Myers Squibb and AstraZeneca, and AstraZeneca has been authorized to perform the developing and marketing of dapagliflozin. It is reported that dapagliflozin can be more successful in maintaining low blood glucose levels than the existing drug of glipizide. However, current test results show that there are still some deficiencies in dapagliflozin in terms of half-life in vivo and absorbency.

Therefore, there is still a need to develop a novel, safe and orally active therapeutic agent for diabetes in the art, in particular developing a novel C-aryl glucoside SGLT2 inhibitor, thereby overcoming deficiencies of the existing therapies.

SUMMARY

In order to overcome the deficiencies of the prior art, the present invention performs structural modification on the existing C-aryl glucoside SGLT2 inhibitors, to improve the half-life, absorption property and pharmacological activity of these drugs, thereby obtaining an active compound of application value. Pharmacological study tests of the present invention show that the obtained novel compound can be used as a more efficient SGLT2 inhibitor, and has advantages of longer half-life and easier absorption etc., thereby having a wide application prospect. In addition, compared to the existing C-aryl glucoside SGLT2 inhibitors, the synthesis method of the compound of the present invention is advantaged in simple operation, mild operation condition and high yield etc., which is more favorable to industrial production.

Therefore, one purpose of the present invention is to provide a novel compound having an activity of inhibitors of sodium-dependent glucose transport protein (SGLT2) or a pharmaceutically acceptable salt, solvate, polymorph, enantiomer or racemic mixture thereof, to overcome the deficiencies in the existing therapies for diabetes and related diseases.

Another purpose of the present invention is to provide a method for preparing the compound or pharmaceutically acceptable salt, solvate, polymorph, enantiomer or racemic mixture thereof.

Yet another purpose of the present invention is to provide use of the compound or pharmaceutically acceptable salt, solvate, polymorph, enantiomer or racemic mixture thereof in preparation of medicaments.

Still another purpose of the present invention is to provide a pharmaceutical composition comprising the compound or pharmaceutically acceptable salt, solvate, polymorph, enantiomer or racemic mixture thereof as a main active ingredient.

Still yet another purpose of the present invention is to provide a method for treating diseases such as diabetes by using the compound or pharmaceutically acceptable salt, solvate, polymorph, enantiomer or racemic mixture thereof or the pharmaceutical composition.

In order to realize the above purposes, the present invention provides the following solutions.

In one aspect, the present invention provides a compound of formula I or a pharmaceutically acceptable salt, solvate, polymorph, enantiomer or racemic mixture thereof,

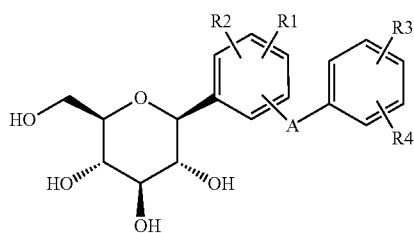

I wherein $R_1$ and $R_2$ are each independently hydrogen, —OH, alkyl, —$CF_3$, —$OCHF_2$, —$OCF_3$ or halogen;
$R_3$ is cycloalkyl, —$OCH_2CF_3$, —$OCH_2CHF_2$, —$OCH_2CH_2F$ or —$OCH_2CH_3$;
$R_4$ is hydrogen, —OH, —O aryl, —$OCH_2$ aryl, alkyl, cycloalkyl, —$CF_3$, —$OCHF_2$, —$OCF_3$, —$OCH_2CF_3$, —$OCH_2CHF_2$, —$OCH_2CH_2F$ or halogen;
A is —$CX_1X_2$, wherein $X_1$ and $X_2$ are each independently H, F and Cl, and when both $X_1$ and $X_2$ are H, $R_3$ is not —$OCH_2CH_3$.

Preferably, the compound of formula I may be as shown in formula Ia:

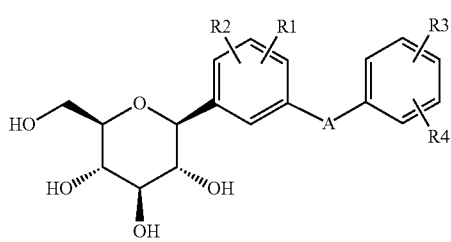

Ia wherein R1 to R4 and A are defined as in claim 1.

More preferably, the compound of formula I may be as shown in formula Ib:

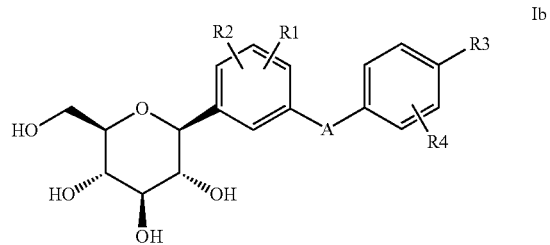

Ib wherein R1 to R4 and A are defined as in claim 1;
Still more preferably, the compound of formula I may be as shown in formula Ic:

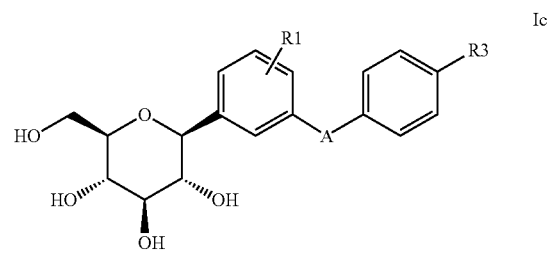

Ic wherein R1, R3 and A are defined as in claim 1
Most preferably, the compound of formula I may be as shown in formula Id:

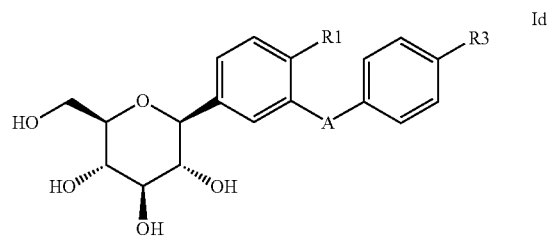

Id wherein R1, R3 and A are defined as in claim 1.
Preferably, R3 in the compound of formula I is —$OCH_2CF_3$, —$OCH_2CHF_2$ or —$OCH_2CH_2F$; and more preferably, R3 is —$OCH_2CF_3$.
Preferably, both $X_1$ and $X_2$ in the compound of formula I may be hydrogen or F.
Preferably, R1 in the compound of formula I is halogen, and more preferably Cl; R2 is preferably hydrogen; and R4 is preferably hydrogen.

According to embodiments of the present invention, the structure of the compound of the present invention is shown as follows:

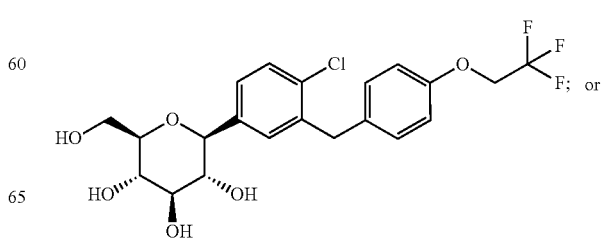

-continued

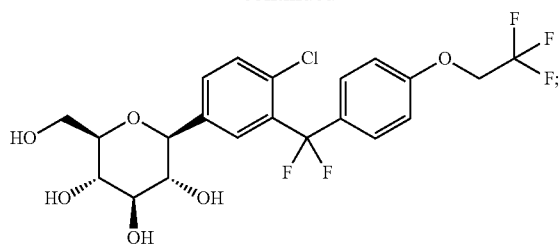

and preferably, the structure of the compound is as follows:

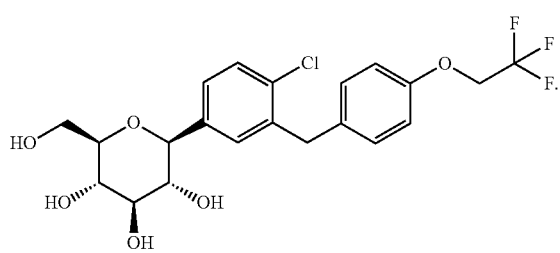 [SMILES: OC[C@H]1O[C@@H](c2ccc(Cl)c(Cc3ccc(OCC(F)(F)F)cc3)c2)[C@H](O)[C@@H](O)[C@@H]1O]

In another aspect, the present invention provides a method for preparing the above compound or the pharmaceutically acceptable salt, solvate, polymorph, enantiomer or racemic mixture thereof, the method comprises the step of reacting a compound of formula IX with a compound of formula X,

IX

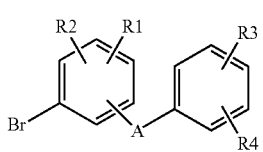

X

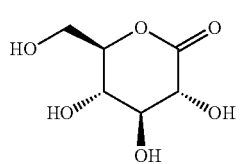

wherein, R1 to R4 and A are defined as above.

Specifically, the method comprises the following steps:

(1) reacting a compound of formula III with trimethylbenzenesulfonyl chloride to generate the compound of formula IX:

III

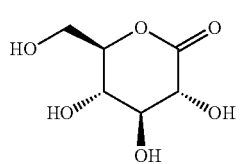

(2) reacting a compound of formula IV with $(COCl)_2$ to generate a compound of formula V:

IV

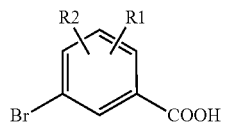

V

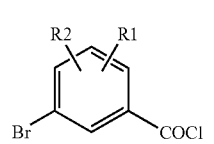

(3) reacting the compound of formula V with a compound of formula VI in the presence of $AlCl_3$ to generate a compound of formula VII:

VI

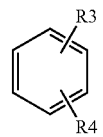

VII

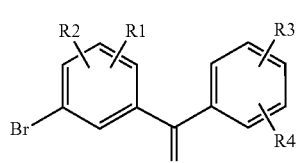

(4) reducing the carbonyl group in the compound of formula VII and/or reacting the carbonyl group to form a halogenated alkyl group to produce the compound of formula X;
(5) reacting the compound of formula IX with the compound of formula X in the presence of n-butyl lithium, methanol and methanesulfonic acid to produce a compound of formula XI:

XI

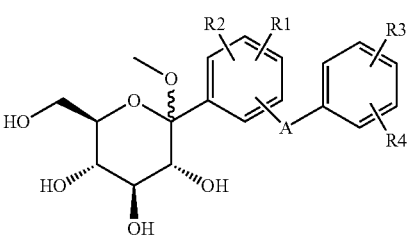

and
(6) converting the compound of formula XI into a compound of formula I in the presence of $Et_3SiH$ and $BF_3.Et_2O$;
wherein R1 to R4 and A are defined as above.

Preferably, in step (1), the compound of formula III is reacted with trimethylbenzenesulfonyl chloride in the presence of N-methylmorpholine.

According to embodiments of the present invention, in step (4), the carbonyl group in the compound of formula VII may be reduced fully, for example, the carbonyl group may be reduced fully in the presence of $Et_3SiH$ and $BF_3.Et_2O$; or in step (4), the carbonyl group may be caused to form a halogenated alkyl group, for example, the carbonyl group may react in the presence of ethane-1,2-dithiol and $BF_3 \cdot 2HOAc$ to form dithiolane, and then the dithiolane is caused to form a halogenated alkyl group by a select-halogen reagent.

According to embodiments of the present invention, the compound represented by the following structure is provided:

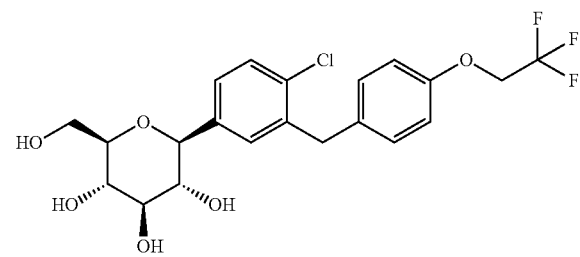 [SMILES: OC[C@H]1O[C@@H](c2ccc(Cl)c(Cc3ccc(OCC(F)(F)F)cc3)c2)[C@H](O)[C@@H](O)[C@@H]1O]

This compound is referred to as compound 2 in other parts of the present specification, and according to embodiments of the present invention, the preparation method of compound 2 comprises the following steps:

Step (1):

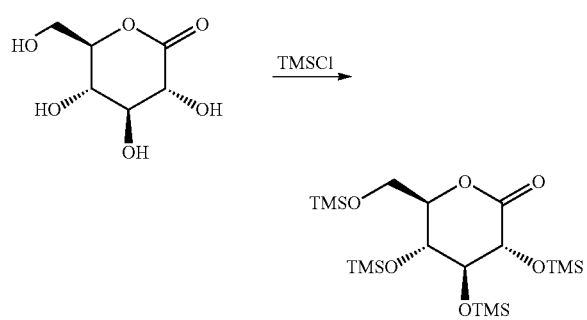

Step (2):

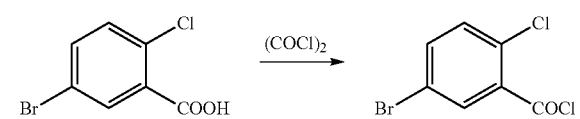 [SMILES: O=C(O)c1cc(Br)ccc1Cl ; "(COCl)2" ; O=C(Cl)c1cc(Br)ccc1Cl]

Step (3):

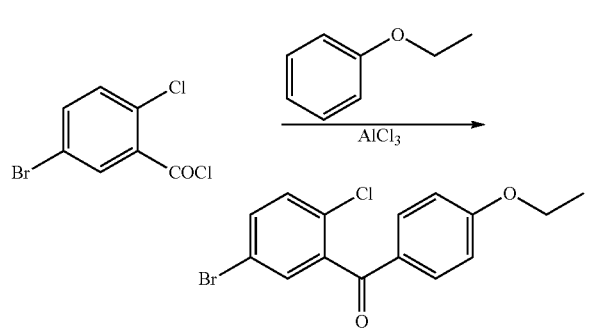

Step (4)-1:

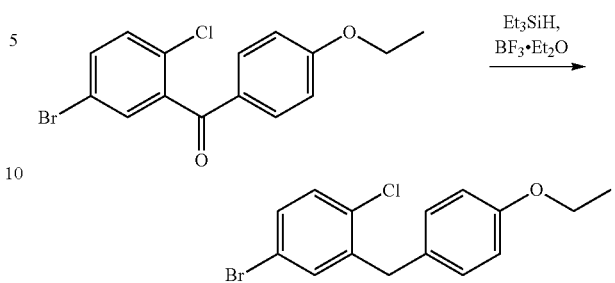

Step (4)-2:

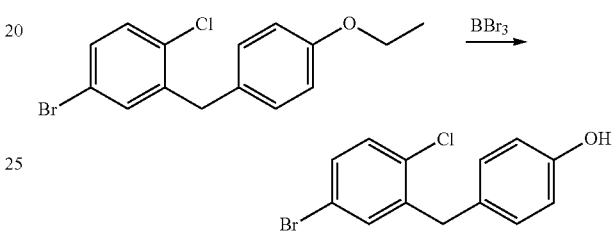

Step (4)-3:

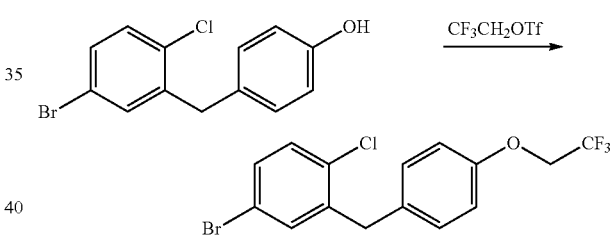

Step (5):

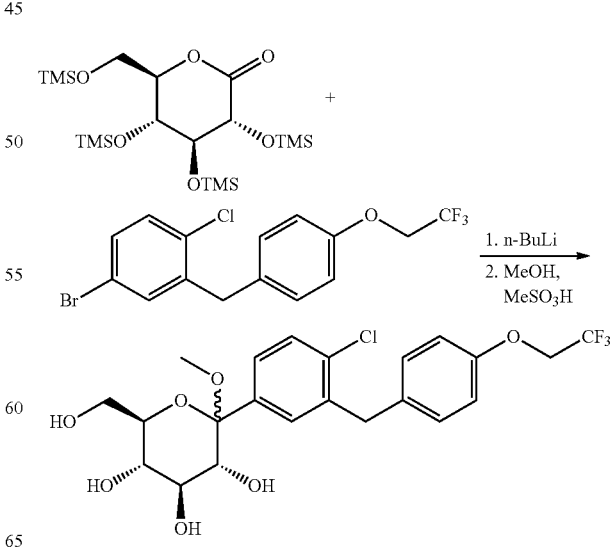

Step (6)-1:
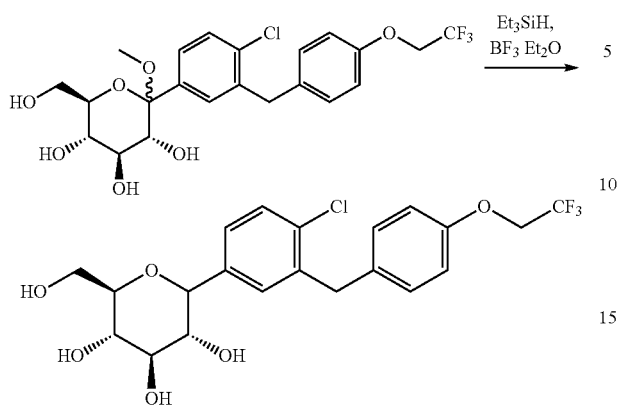
Step (6)-2:
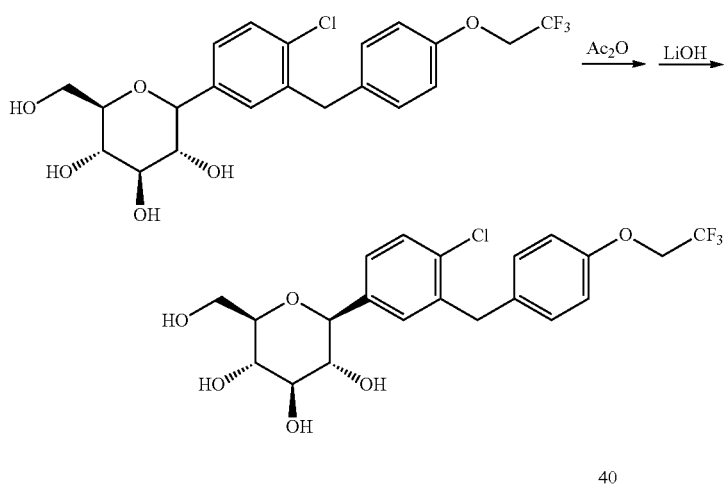
According to embodiments of the present invention, the compound represented by the following structure is further provided:
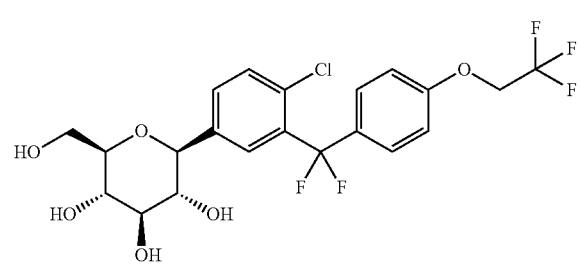 [SMILES: OC[C@H]1O[C@@H](c2ccc(Cl)c(C(F)(F)c3ccc(OCC(F)(F)F)cc3)c2)[C@H](O)[C@@H](O)[C@@H]1O]
This compound is referred to as compound 3 in other parts of the present specification, and according to embodiments of the present invention, the preparation method of compound 3 comprises the following steps:
Step (1):
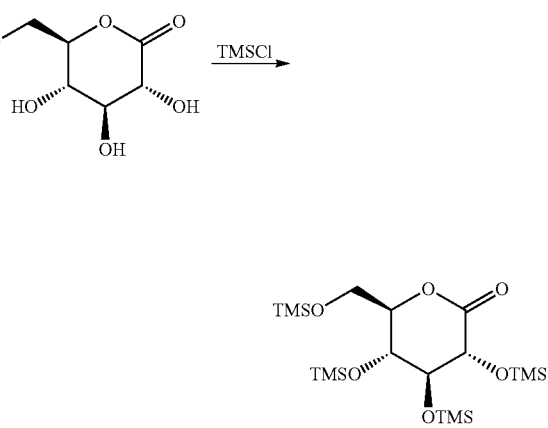
Step (2):
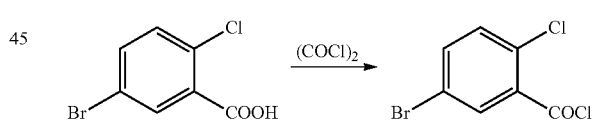
Step (3):
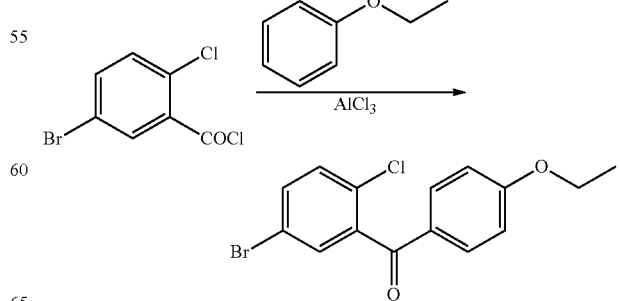

Step (4)-1:

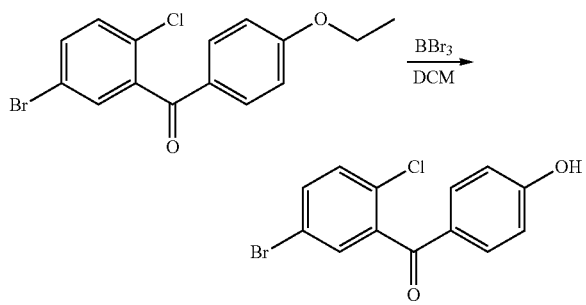

Step (4)-2:

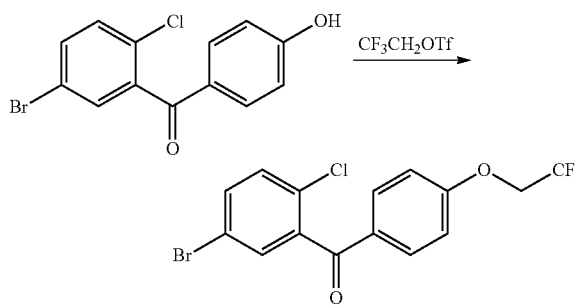

Step (4)-3:

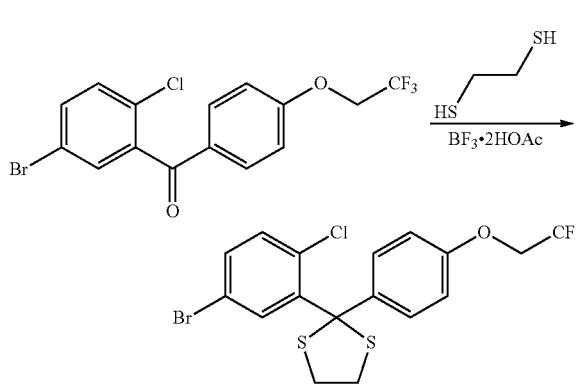

Step (4)-4:

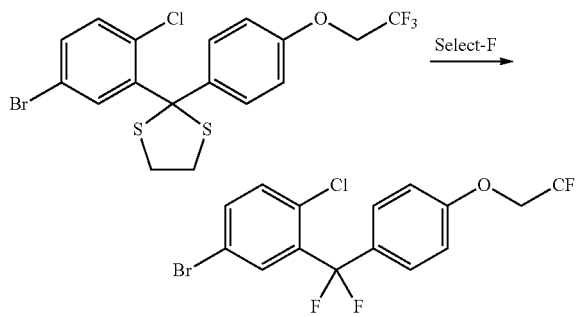

Step (5):

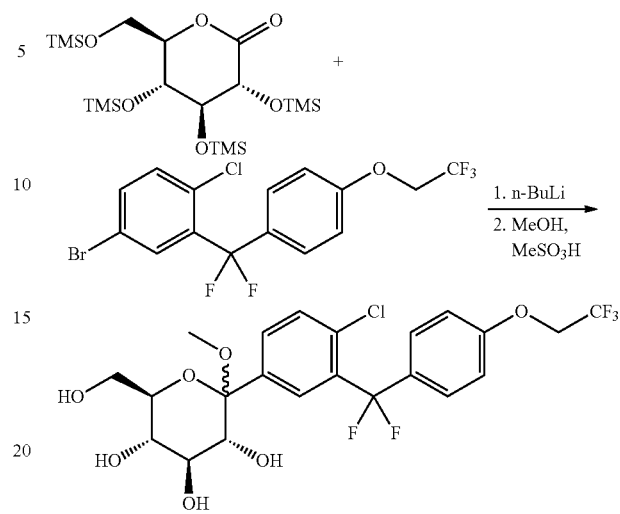

Step (6):

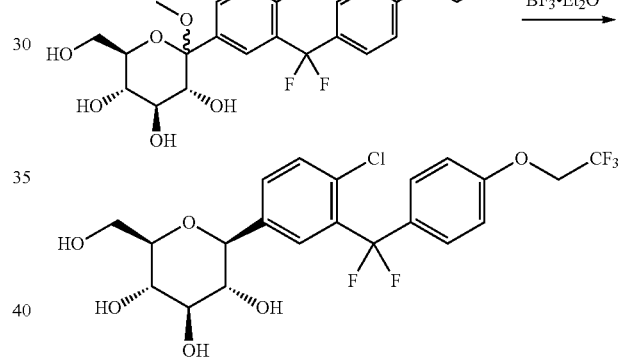

In another aspect, the present invention provides use of the above compound or the pharmaceutically acceptable salt, solvate, polymorph, enantiomer or racemic mixture thereof in the preparation of medicaments of Daryl glucoside SGLT2 inhibitors. Experiments prove that the compound of the present invention can function as an SGLT2 inhibitor, and therefore can be prepared into corresponding medicaments of SGLT2 inhibitors for clinical treatment or research.

In yet another aspect, the present invention provides use of the above compound or the pharmaceutically acceptable salt, solvate, polymorph, enantiomer or racemic mixture thereof in the preparation of medicaments for treating, preventing or delaying the following diseases: diabetes, hyperglycemia, hyperinsulinemia, hyperlipidemia, obesity, X syndrome, hypertriglyceridemia, atherosclerosis, hypertension or diabetic complication.

Preferably, the diabetic complication is diabetic retinopathy, diabetic neuropathy and/or diabetic nephropathy; and preferably, the disease is diabetes, and is more preferably type II diabetes.

In still another aspect, the present invention further provides a pharmaceutical composition comprising the compound or the pharmaceutically acceptable salt, solvate, polymorph, enantiomer or racemic mixture thereof provided by the present invention, and a pharmaceutically acceptable excipient.

The pharmaceutical composition may be in any dosage form for clinical application, such as tablet, suppository, dispersible tablet, enteric-coated tablet, chewable tablet, orally disintegrating tablet, capsule, sugar-coated agent, granule, dry powder, oral solution, small needle for injection, lyophilized powder or large volume parenteral for injection.

Based on the specific dosage and administration route, the pharmaceutically acceptable excipient of the pharmaceutical composition may comprise one or more of the following excipients: diluents, solubilizers, disintegrating agents, suspending agents, lubricants, binders, fillers, flavoring agents, sweeteners, antioxidants, surfactants, preservatives, wrapping agents and pigments, etc.

Further, the pharmaceutical composition may also comprise other therapeutic agents, such as one or more medicaments selected from: anti-diabetic agents, anti-obesity agents, anti-hypertensive agents, anti-atherosclerotic agents and lipid-lowering agents; and preferably, the pharmaceutical composition may further comprise an anti-diabetic agent.

In still yet another aspect, the present invention provides a method for treating, preventing or delaying the following diseases: diabetes, hyperglycemia, hyperinsulinemia, hyperlipidemia, obesity, X syndrome, hypertriglyceridemia, atherosclerosis, hypertension or diabetic complication, and the method comprises: administering to a patient in need thereof a therapeutically effective amount of the compound or the pharmaceutically acceptable salt, solvate, polymorph, enantiomer or racemic mixture thereof provided by the present invention, or the pharmaceutical composition of the present invention. Furthermore, the compound or the pharmaceutically acceptable salt, solvate, polymorph, enantiomer or racemic mixture thereof provided by the present invention, or the pharmaceutical composition of the present invention may be co-administered with other therapies or therapeutic agents.

Doses of the compound or pharmaceutical composition needed for implementing functions such as treating, preventing or delaying usually depend on the particular compound to be administered, patient, specific disease or disorder and severity thereof, route and frequency of administration and so on, and need to be determined by the attending doctor in accordance with specific conditions. For example, when the compound or pharmaceutical composition of the present invention is administrated orally, the dosage may be 1-100 mg/day, and preferably 2-50 mg/day, more preferably 10 mg/day; and the dose may be administrated for 1-3 times daily, and preferably once daily.

In summary, the present invention provides a novel compound having an activity of sodium-dependent glucose transport protein (SGLT2) inhibitors. Experiments prove that compared with the existing. C-aryl glucoside SGLT2 inhibitors, the compound of the present invention has longer half-life and higher oral absorption rate, making it more suitable to be prepared into drugs in a variety of dosage forms, especially suitable to be prepared into drugs in oral administration for treatment of diabetes, in particular type II diabetes.

BRIEF DESCRIPTION OF THE DRAWINGS

Hereinafter, embodiments of the present invention will be described with reference to the accompanying drawings in detail:

FIG. 2 shows results of the glucose tolerance test in Example 5, wherein 2A represents blood glucose level (mg/mL); 2B represents ΔAUC value (mg/dL*hr) of each group, where group 1 is blank solution, group 2 is compound 1, group 3 is compound 2, and group 4 is compound 3;

FIG. 3 shows blood glucose test results of the glucose tolerance test in Example 6, which are represented by blood glucose level (mg/mL);

DETAILED DESCRIPTION OF PREFERRED EMBODIMENTS

Figure 1:
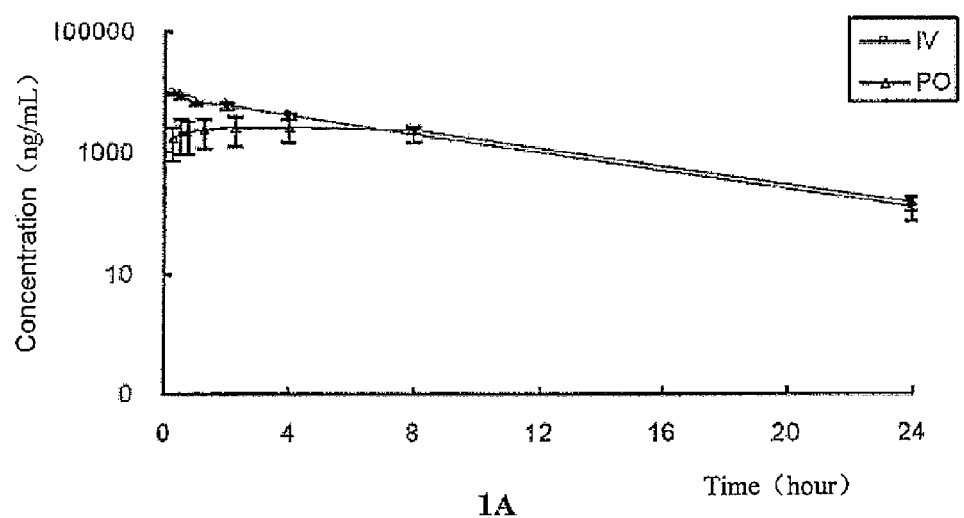
FIG. 1 shows the pharmacokinetic curves of the compounds of Example 3, wherein 1A represents compound 1, 1B represents compound 2, 1C represents compound 3.
Figure 1:
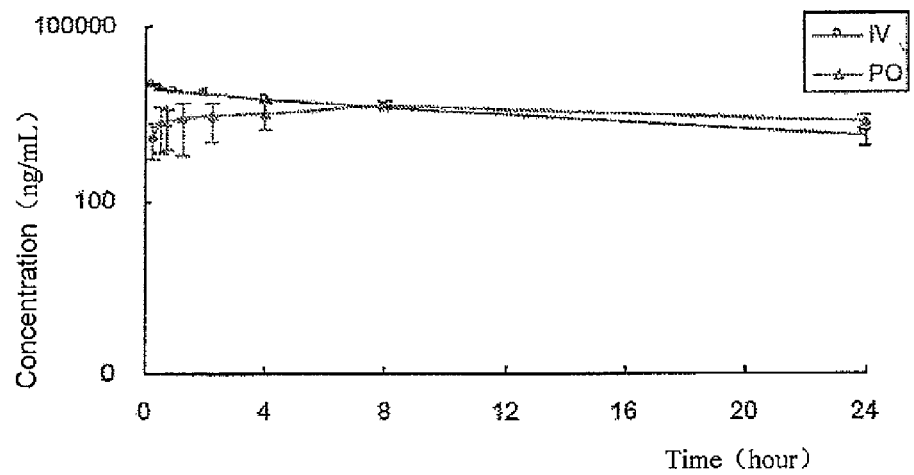

The present invention will be further described in detail in combination with the embodiments hereinafter. It should be noted that the embodiments provided are only used to illustrate the present invention, rather than limiting the scope of the present invention.

Experimental methods in the following embodiments, if no special instructions, are all conventional methods. Medicinal materials, reagents and other materials used in the following examples, if no special instructions, can be purchased from the conventional biochemical reagent stores or pharmaceutical trading enterprises.

EXAMPLE 1

Preparation of Compound 2 of the Present Invention

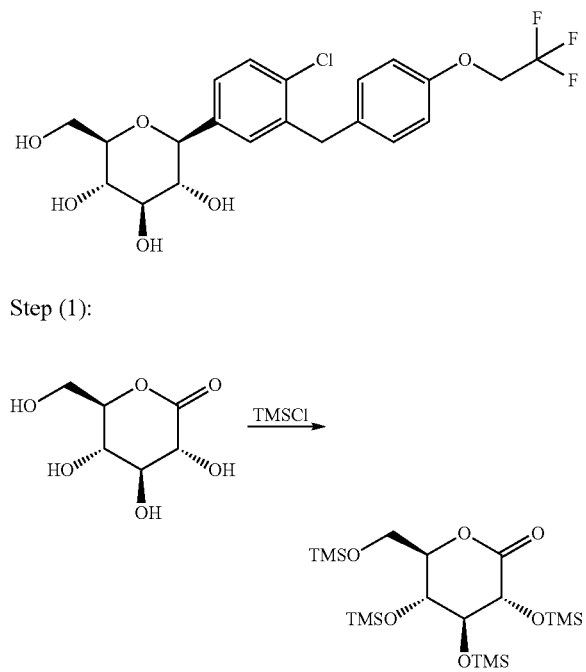

Step (1):

At −7° C., TMSCl (71 mL) was added into a solution of (3R,4S,5S,6R)-3,4,5-trihydroxy-6-(hydroxymethyl)tetrahydro-2H-pyran-2-one (14.2 g) and N-methylmorpholine (80 mL) in dry THF (120 mL), and then the mixture was slowly warmed up to room temperature and stirred overnight. At 10° C., toluene (160 mL) and H$_2$O (300 mL) were poured into the mixture, and then the organic phase was washed with H$_2$O (120 mL), 1M HCl (150 mL×4) and brine (120 mL). The organic phase was dried over Na$_2$SO$_4$, and concentrated to obtain the crude product, then the crude product was purified by silica-gel column chromatography (PE/EA=10/1) to obtain 30 g of (3R,4S,5R,6R)-3,4,5-tris(trimethylsilyloxy)-6-((trimethylsilyloxy)methyl)tetrahydro-2H-pyran-2-one.

Step (2):

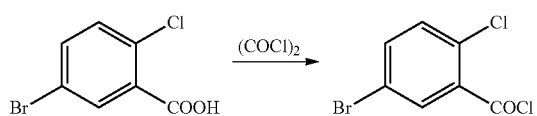

At room temperature, (COCl)$_2$ (15 mL) was added dropwise into a solution of 5-bromo-2-chlorobenzoic acid (40 g) in DCM (300 mL). Then DMF (0.5 mL) was added into the solution, and the mixture was stirred at room temperature for overnight. The solution was concentrated directly to obtain the crude product of 5-bromo-2-chlorobenzoyl chloride, which was directly used in the next step.

Step (3):

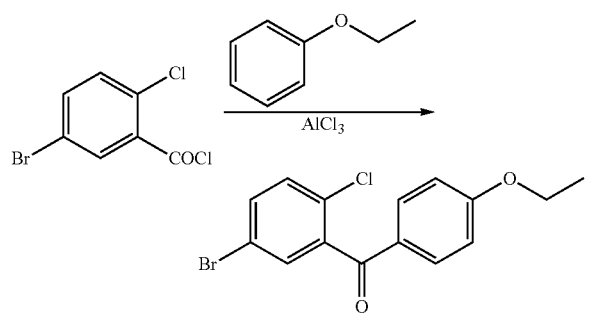

At −5-0° C., ethoxybenzene (20.5 g) and AlCl$_3$ (22.3 g) were added into a solution of 5-bromo-2-chlorobenzoyl chloride (from step 2) in dry DCM (200 mL). Then the mixture was stirred at −5-0° C. for 1 h. The mixture was poured into ice-H$_2$O (200 mL) and extracted with DCM. The organic phase was washed with 1M HCl, H$_2$O, 1M NaOH and brine. And the organic phase was concentrated, and the crude was purified by silica-gel column chromatography (PE/EA=80/1-40/1), to obtain 30 g of (5-bromo-2-chloro phenyl)(4-ethoxyphenyl)methanone.

Step (4)-1:

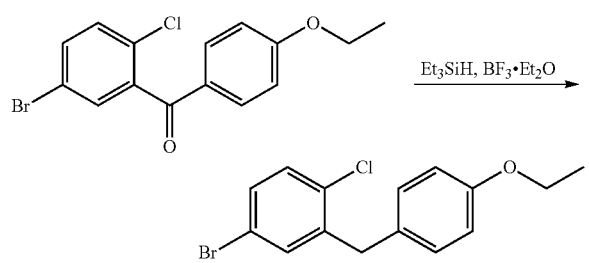

At −20° C., BF$_3$.Et$_2$O (0.75 mL) was added slowly into a solution of (5-bromo-2-chlorophenyl)(4-ethoxyphenyl)methanone (2 g) and Et$_3$SiH (2 mL) in dry DCM (5 mL) and CH$_3$CN (10 mL), then the mixture was stirred at room temperature for overnight. 7M KOH was slowly added into the mixture, and then the mixture was extracted with DCM, the organic phases were combined, dried over Na$_2$SO$_4$ and concentrated to obtain the crude product. The crude product was purified by silica-gel column chromatography (PE/EA=10/1) to obtain 3 g of 4-bromo-1-chloro-2-(4-ethoxybenzyl)benzene.

Step (4)-2:

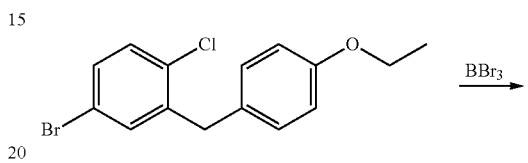

At −78° C., BBr$_3$ (0.26 mL) was added into a solution of 4-bromo-1-chloro-2-(4-ethoxybenzyl)benzene (0.3 g) in dry DCM, then the mixture was stirred at 0° C. for 1 h, and stirred at room temperature for 24 h. MeOH was slowly added into the mixture. Then the mixture was extracted with DCM, and the organic phases were combined and washed with 2M HCl and brine, then dried over Na$_2$SO$_4$ and concentrated, to obtain 2.5 g crude product which was directly used in the next step.

Step (4)-3:

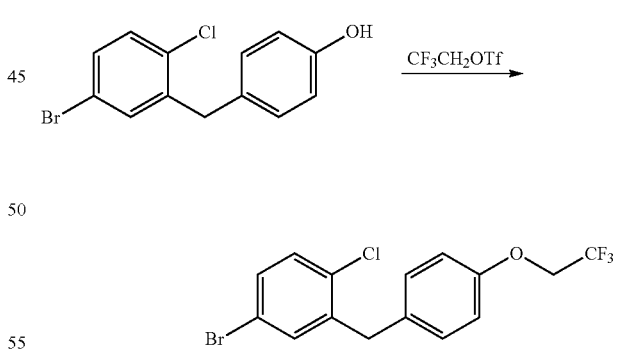

At 0° C., NaH (0.43 g) was added into a solution of 4-(5-bromo-2-chloro-benzyl)-phenol (1.6 g) in DMF (20 mL), then the mixture was stirred at room temperature for 2 h. The mixture was poured into H$_2$O, and 2M HCl was added to adjust the pH to 6-7, and then the mixture was extracted with EtOAc. The organic phase was washed with brine, dried over Na$_2$SO$_4$, and concentrated to obtain the crude product, then the crude product was purified by silica-gel column chromatography (PE/EA=100/1) to obtain 1.4 g of 4-bromo-1-chloro-2-[4-(2,2,2-trifluoro-ethoxy)-benzyl]benzene.

Step (5):

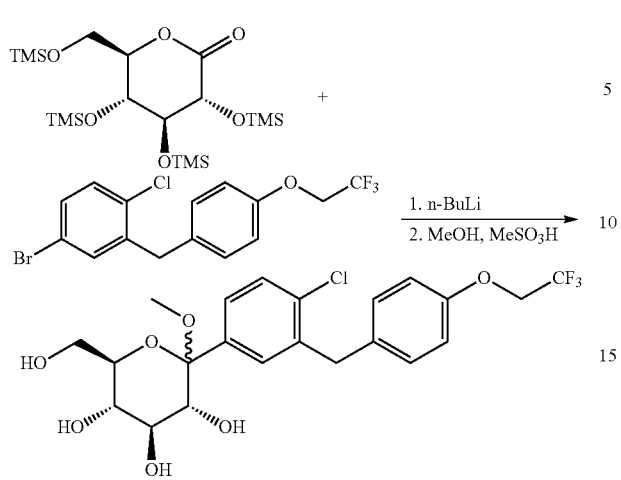

At −78° C., 0.93 mL (2.5M, 2.3 mmol) n-BuLi was added dropwise into the mixture of 4-bromo-1-chloro-2-[4-(2,2,2-trifluoro-ethoxy)-benzyl]benzene (800 mg, 2.1 mmol) in toluene/THF (2 mL/2 mL). After 30 minutes, at −78° C. the mixture was added with (3R,4S,5R,6R)-3,4,5-tris(trimethylsilyloxy)-6-(((trimethylsilyloxy)methyl)tetrahydro-2H-pyran-2-one (932 mg, 2.1 mmol) in 3 mL toluene and stirred for 30 minutes. Then at −78° C. MsOH (500 mg) in MeOH (5 mL) was added into the mixture. Then the mixture was slowly warmed up to room temperature and stirred at room temperature overnight. The mixture was quenched with saturated NaHCO₃ aqueous solution (20 mL). The aqueous layer was extracted with EtOAc (20 mL×3), dried over Na₂SO₄, and then concentrated under vacuum, to obtain 900 mg of crude product, which was directly used in the next step.

Step (61)-1:

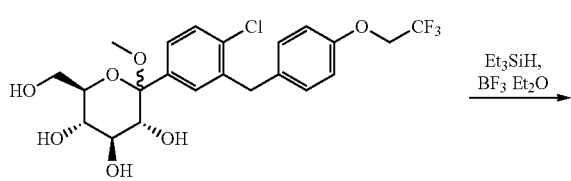

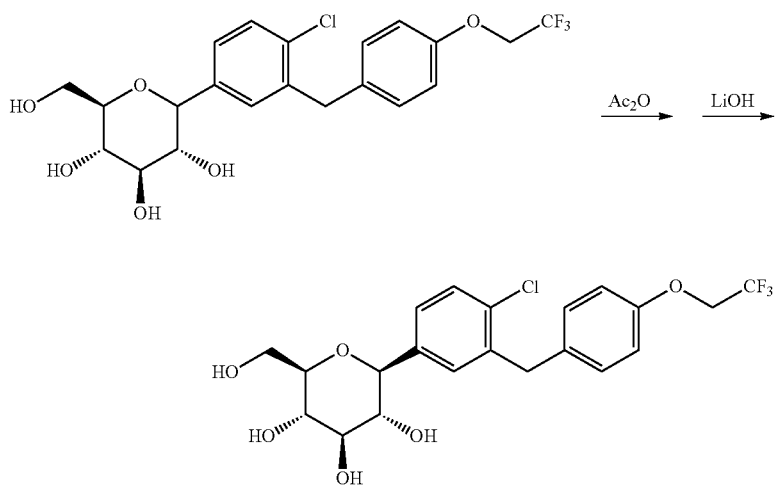

At −10° C., Et₃SiH was added into the mixture of 2-(4-chloro-3-{[4-(2,2,2-trifluoroethoxy)phenyl]methyl}phenyl)-6-(hydroxymethyl)-2-methoxyl-2H-3,4,5,6-tetrahydropyran-3,4,5-triol in DCM/MeCN (2 mL/2 mL), then BF₃.OEt₂ (0.4 mL) was added into the mixture below −10° C. At 0° C. the mixture was stirred for 5 h. Then the mixture was quenched with saturated NaHCO₃ aqueous solution (5 mL), extracted with ErOH (20 mL×4), dried over Na₂SO₄, and concentrated under vacuum to obtain 800 mg of desired yellow solid, which was directly used in the next step.

Step (6)-2:

At 0° C., Ac₂O was added dropwise into the mixture of DMAP (24 mg), pyridine (6 mL) and 2-(4-chloro-3-{[4-(2,2,2-trifluoroethoxy)phenyl]methyl}phenyl)-6-(hydroxymethyl)-2H-3,4,5,6-tetrahydropyran-3,4,5-triol (900 mg) in DCM. The mixture was stirred at room temperature for 30 minutes. TLC indicated no starting material remained. The mixture was treated with saturated NaHCO₃ aqueous solution (20 mL), and extracted with DCM (50 mL×1). The combined DCM was washed with 1N HCl (50 mL) and brine (50 mL), dried over Na₂SO₄, and concentrated to obtain the crude product, then the crude product was recentralized with pure EtOH, to obtain 499 mg trans-product as white solid (cis-product was dissolved in EtOH, and two isomers can be separated on TLC).

The mixture of LiOH.H₂O (166 mg, 3.9 mmol) and 2-(4-chloro-3-{[4-(2,2,2-trifluoroethoxy)phenyl]methyl}phenyl)-6-(hydroxymethyl)-2-methoxy-2H-3,4,5,6-tetrahydropyran-3,4,5-triol (499 mg, 0.79 mmol) in THF/H₂O (5 mL/5 mL) was stirred overnight at room temperature. TLC indicated completion of reaction. The mixture was extracted with EtOAc (50 mL×2), dried over Na₂SO₄, and concentrated under vacuum to obtain the crude product, and the crude product was purified by preparative TLC (DCM/MeOH=10/1) to obtain 165 ring of target compound as white solid.

Molecular weight: 462.9.

$^1$H NMR (400 MHz, MeOH-d$_4$): δ 7.30-7.38 (m, 3H), 7.18 (d, d, J=8.8 Hz, 2H), 6.91-6.94 (m, 2H), 4.46-4.52 (m, 2H), 4.07-4.13 (m, 3H), 3.91-3.92 (m, 1H), 3.72-3.73 (m, 1H), 3.40-3.48 (m, 3H), 3.28-3.30 (m, 1H).

EXAMPLE 2

Preparation of Compound 3 of the Present Invention

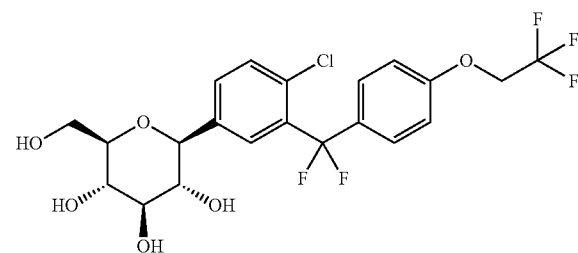 [SMILES: OC[C@H]1O[C@@H](c2ccc(Cl)c(C(F)(F)c3ccc(OCC(F)(F)F)cc3)c2)[C@H](O)[C@@H](O)[C@@H]1O]

Step (1):

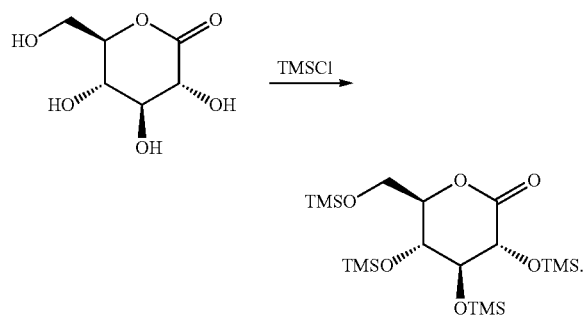

This step is the same as step (1) in Example 1.

Step (2):

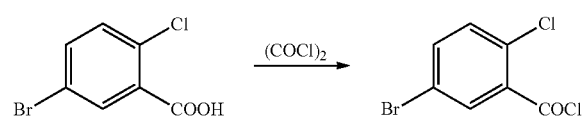 [SMILES: O=C(O)c1cc(Br)ccc1Cl ; "(COCl)2" ; O=C(Cl)c1cc(Br)ccc1Cl]

This step is the same as step (2) in Example 1.

Step (3):

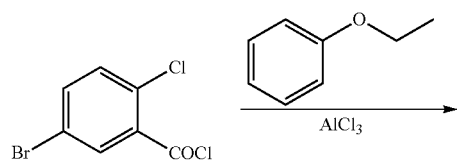

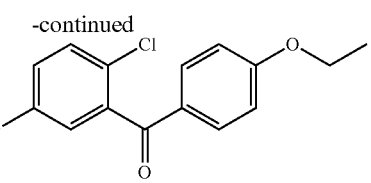

This step is the same as step (3) in Example 1.

Step (4)-1:

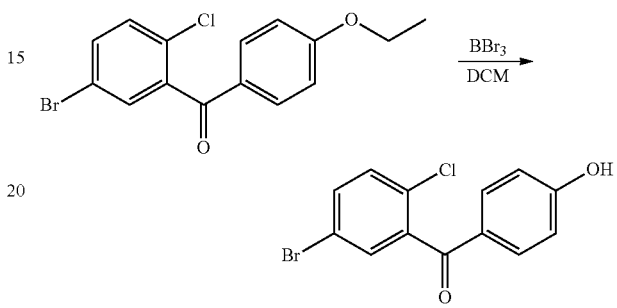

At −78° C., BBr$_3$ (4.4 g, 3 eq) was added slowly into a solution of (5-bromo-2-chlorophenyl)(4-ethoxyphenyl)methanone in dry DCM, then the mixture was stirred for 1 h at 0° C. and stirred for 24 h at room temperature. TLC (PE/EA=1/1) indicated that the starting materials reacted completely. Saturated NaHCO$_3$ aqueous solution was added slowly into the mixture, to adjust the pH to 8-9. Then the mixture was extracted with DCM, and the organic phases were combined, dried over Na$_2$SO$_4$ and concentrated to obtain 2.5 g crude product, which was directly used in the next step.

Step (4)-2:

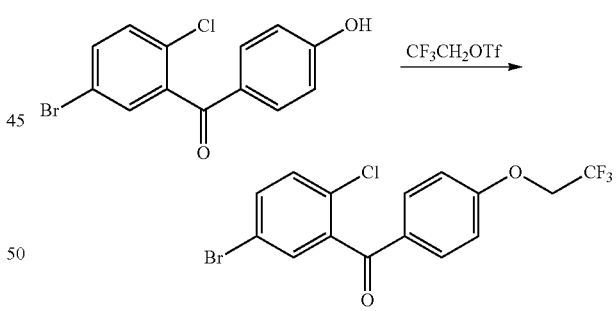

At 0° C., NaH (1.6 g) was added into a solution of (5-bromo-2-chlorophenyl)(4-hydroxyphenyl)methanone (6.2 g) in dry DMF (40 mL). The mixture was stirred at room temperature for 1 h. Then CF$_3$CH$_2$OTf (9.3 g) was slowly added into the mixture at 0° C. The mixture was stirred at room temperature for 0.5 h. Saturated NH$_4$Cl aqueous solution was added slowly into the mixture, and the mixture was extracted with EtOAc. The organic phases were combined, dried over Na$_2$SO$_4$ and concentrated to obtain the crude product, then the crude product was purified by silica-gel column chromatography (PE/EA=20/1) to obtain 5.0 g of (5-bromo-2-chlorophenyl)(4-(2,2,2-trifluoroethoxy)phenyl)methanone.

Step (4)-3:

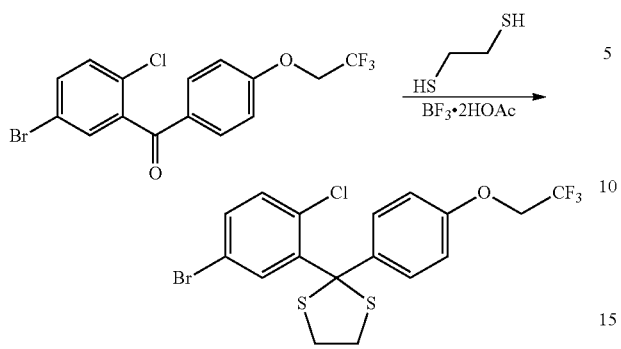

At 0° C., ethane-1,2-dithiol (3 mL) and BF$_3$.2HOAc (4.8 mL) were added into a solution of (5-bromo-2-chlorophenyl)(4-(2,2,2-trifluoroethoxy)phenyl)methanone (5.0 g) in dry DCM. The mixture was stirred at room temperature for 12 hours. The mixture was added with saturated Na$_2$CO$_3$ aqueous solution and then extracted with DCM. The organic phases were combined, dried over Na$_2$SO$_4$, and concentrated to obtain the crude product, then the crude product was purified by silica-gel column chromatography (PE/EA=200/1) to obtain 4 g of 2-(5-bromo-2-chlorophenyl)-2-(4-(2,2,2-trifluoroethoxy)phenyl)-1,3-dithiolane.

Step (4)-4:

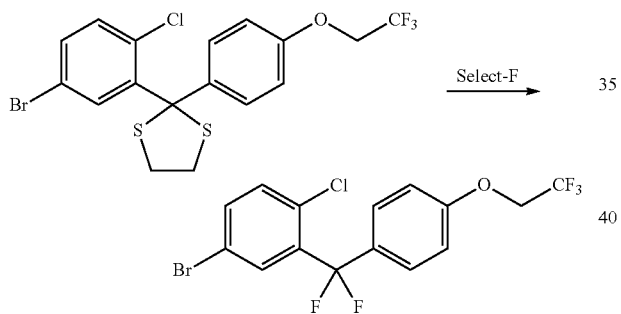

At 0° C., hydrogen fluoride-pyridine (40 mL) and the Select-Fluoro reagent (8.4 g) were added into a solution of 2-(5-bromo-2-chlorophenyl)-2-(4-(2,2,2-trifluoroethoxy)phenyl)-1,3-dithiolane (4 g) in dry DCM (40 mL) in a plastic bottle. Then the mixture was stirred at 0° C. for 2 hours. The solution was extracted with saturated NaHCO$_3$ aqueous solution and DCM. The organic phase was combined, dried over Na$_2$SO$_4$, and then concentrated to obtain the crude product, then the crude product was purified by silica-gel column chromatography (PE/EA=500/1) to obtain 3.2 g of 4-bromo-1-chloro-2-(difluoro(4-(2,2,2-trifluoroethoxy)phenyl)methyl)benzene.

Step (5):

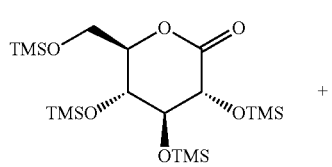
+

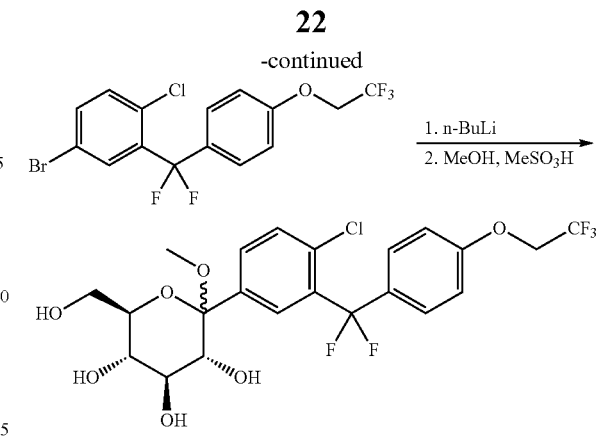

At −78° C., n-BuLi (2.5 M, 0.85 mL) was slowly added into a mixture of 4-bromo-1-chloro-2-{difluoro-[4-(2,2,2-trifluoro-ethoxy)-phenyl]-methyl}benzene (0.8 g) in THF/toluene (6 mL, the ratio of THF to toluene is 1/2). After 30 minutes, (3R,4S,5R,8R)-3,4,5-tris(trimethylsilyloxy)-6-((trimethylsilyloxy)methyl)tetrahydro-2H-pyran-2-one (0.9 g) in toluene (2 ml) was added into the mixture at −78° C. After another 30 minutes, MsOH (0.38 g) in MeOH (5 mL) was added into the mixture at −78° C. The mixture was slowly warmed up to room temperature and stirred overnight. Then the mixture was quenched with saturated NaHCO$_3$ aqueous solution, and extracted with EtOAc. The organic phase was dried over Na$_2$SO$_4$, and concentrated to obtain 900 mg of crude product, which was directly used in the next step.

Step (6):

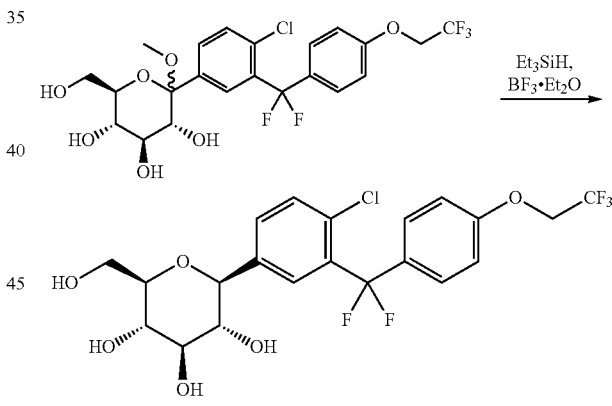

At 0° C., Et$_3$SiH (1 mL) was added into a solution of the crude product (from step 6, 0.9 g) in DCM/THF (4 mL, the ratio of DCM to THF is 1/1), then BF$_3$.Et$_2$O (0.8 mL) was added into the mixture at −10° C., and the mixture was stirred at 0° C. for 5 h. Then the mixture was quenched with saturated NaHCO$_3$ aqueous solution (5 mL), and extracted with EtOAc (20 mL×3). The organic phase was dried over Na$_2$SO$_4$, and concentrated to obtain the crude product, and the crude product was purified by preparative TLC to obtain 60 mg of target compound.

Molecular weight: 498.8.

$^1$H NMR (400 MHz, MeOH-d$_4$): δ 7.95 (d, J=2.0 Hz, 1H), 7.58 (dd, J=2.0 Hz, 8.4 Hz, 1H), 7.30-7.37 (m, 3H), 6.95 (d, J=8.8 Hz, 2H), 4.65 (d, J=5.2 Hz, 1H), 4.44-4.48 (m, 2H), 4.20 (d, J=7.2 Hz, 1H), 3.73-3.79 (m, 2H), 3.54-3.58 (m, 2H).

EXAMPLE 3

Stability Test In Vitro

In this embodiment, metabolic stability in vitro of compound 2 and compound 3 of the present invention were detected, and compared with that of the known compound 1.

Test compounds: compound 1, compound 2 and compound 3;

Control compound: verapamil.

Microsomes: human liver microsomes (HMMC; PL050B) and male rat liver microsomes (RTMC; RT046), which were purchased from CellzDirect (Invitrogen) and stored at −80° C. before use.

Method:

1) Master solution was prepared according to Table 1, and then the test compounds and control compound were added into the master solution, with the final concentration of these compounds in the reaction system being 2 μM. Then the mixed solution was preheated at 37° C. for 2 minutes.

TABLE 1

Preparation of master solution

| Ingredient | Concentration of stock solution | Volume | Final concentration |
|---|---|---|---|
| Microsome (HMMC or RTMC) | 5 mg/mL | 50 μL | 0.5 mg/mL |
| MgCl$_2$ solution | 50 mM | 50 μL | 5 mM |
| Phosphate buffer | 200 mM | 250 μL | 100 mM |
| Ultrapure water | — | 95 μL | |

2) NADPH was added into the mixed solution with the final concentration of NADPH being 1 mM, and then the reaction system was incubated at 37° C. The blank control was also added with the same volume of ultrapure water instead of NADPH.

3) 50 μL aliquots were taken out from the reaction system at 0, 15, 30, 45 and 60 minutes, and added with 3 volumes of cold methanol to terminate the reaction. The aliquot was centrifugated for 10 minutes under 16000 g to precipitate proteins. 100 μL of supernatant was used for LC/MS/MS analysis, to determine the amounts of the remaining test compounds and the control compound. The aliquots were detected in duplicate.

The instruments and conditions for LC analysis were as follows:

Shimadzu (Degasser DGU—20A3, Solvent Delivery Unit LC—20ADXR, System Controller CBM—20A, Column Oven CTO—10ASVP), CTC Analytics HTC PAL—XT System Column: Phenomenex 5μ C 18 (2) (2.0×50 mm)

Mobile phase: 0.1% formic acid aqueous solution (B) and 0.1% formic acid—acetonitrile (A); procedure of elution: 0-2 min, mobile phase A of 5-100%, and mobile phase B of 95-0%; 2-2.2 min, mobile phase A of 100%, and mobile phase B of 0%; 2.2-2.4 min, mobile phase A of 100-5%, mobile phase B of 0-95%; 2.4-3 min, mobile phase A of 5%, and mobile phase B of 95%.

Flow rate: 0.5 mL/min;

Column temperature: 25° C.;

Volume of sample: 10 μL.

The instrument and conditions for MS/MS analysis were as follows:

AB API4000 LC/MS/MS instrument

Source: Turbo spray

Ionization mode: ESI

Type of scan: MRM

Collision gas: 6 L/min; curtain gas: 30 L/min; atomized gas: 50 L/min; auxiliary gas: 50 L/min; temperature: 500° C.; spray voltage: 4500 v.

Test Results:

Test results of stability in vitro of compound 1, compound 2, compound 3 and the control compound of verapamil in human or rat liver microsome system containing NADPH are shown in Table 2 and Table 3.

TABLE 2

Residual percentage (%) of compounds in human liver microsome at different time

| | Sampling time (minute) | | | | |
|---|---|---|---|---|---|
| Compound | 0 | 15 | 30 | 45 | 60 |
| Verapamil | 100.00 | 61.67 | 41.87 | 29.31 | 22.38 |
| Compound 1 | 100.00 | 100.36 | 102.10 | 101.77 | 93.93 |
| Compound 2 | 100.00 | 80.84 | 78.78 | 76.73 | 75.34 |
| Compound 3 | 100.00 | 105.74 | 98.43 | 101.18 | 97.89 |

TABLE 3

Residual percentage (%) of compounds in rat liver microsome at different time

| | Sampling time (minute) | | | | |
|---|---|---|---|---|---|
| Compound | 0 | 15 | 30 | 45 | 60 |
| Verapamil | 100.00 | 33.09 | 15.52 | 9.78 | 4.48 |
| Compound 1 | 100.00 | 88.37 | 90.68 | 83.66 | 83.63 |
| Compound 2 | 100.00 | 88.20 | 94.51 | 91.65 | 88.27 |
| Compound 3 | 100.00 | 99.00 | 92.49 | 97.25 | 108.11 |

It can be seen from the data of Table 2 and Table 3 that, in human and rat liver microsome systems containing NADPH, the control compound verapamil decomposed rapidly. The existing SGLT2 inhibitor compound 1 remained to substantially stable in human and rat liver microsomes, and there was still over 80% of compound 1 retained after 60 minutes. In contrast, the stability of compound 2 and compound 3 of the present invention in human and rat liver microsomes are better than that of compound 1, and compound 3 has better stability.

EXAMPLE 4

Pharmacokinetic Test In vivo

Pharmacokinetics in vivo of compound 2 and compound 3 of the present invention and the known compound 1 were detected in this Example.

Method:

Compound 1, compound 2 and compound 3 were respectively dissolved in blank solution (5% 1-methyl-2-pyrrolidinone, 20% PEG-400 and 20 mM sodium diphosphate) in a concentration of 10 g/L.

Experimental animals are male SD rats of 6-8 weeks old, with weight of 190-215 g, which were purchased from Beijing Vital River Laboratory Animal Technology Co., Ltd. The SD rats were randomly divided into seven groups based on body weight, each group containing three rats. Wherein group 1 is the blank control group in which the blank solution was administrated intravenously. Doses and routes of administration of the rats in each group are shown in Table 4.

TABLE 4

Grouping and administration for pharmacokinetic test

| Group | Drug | Dose of drug (mg/kg) | Route | Number |
|---|---|---|---|---|
| Group 1 | Blank solution | 0 | Administrated orally | 3 |
| Group 2 | Compound 1 | 10 | Administrated orally | 3 |
| Group 3 | Compound 1 | 10 | Administrated intravenously | 3 |
| Group 4 | Compound 2 | 10 | Administrated orally | 3 |

TABLE 4-continued

Grouping and administration for pharmacokinetic test

| Group | Drug | Dose of drug (mg/kg) | Route | Number |
|---|---|---|---|---|
| Group 5 | Compound 2 | 10 | Administrated intravenously | 3 |
| Group 6 | Compound 3 | 10 | Administrated orally | 3 |
| Group 7 | Compound 3 | 10 | Administrated intravenously | 3 |

Before the pharmacokinetic test, the SD rats were fasted for 16 hours, and then administrated intravenously (1 mL/kg; 10 mg/kg) or orally (1 mL/kg; 10 mg/kg) with single dose of the compound or blank solution according to Table 4. After administration 200 uL blood samples were collected regularly through jugular vein puncture, wherein for the group of animals administered intravenously, blood samples were collected at 0 minute, 15 minutes, 30 minutes, 1 hour, 2 hours, 4 hours, 8 hours and 24 hours after administration; for the group of animals administered orally, blood samples were collected at 0 minute, 15 minutes, 30 minutes, 45 minutes, 75 minutes, 135 minutes, 4 hours, 8 hours and 24 hours after administration. The blood samples were collected in a sample tube with EDTA, and immediately centrifuged under 4000 rpm for 0.5 minutes at 4° C., and then the plasma was transferred to another sample tube and stored at −20° C.

The method and instruments for pharmacokinetics test of samples were as follows:
HPLC: Shimadzu (DGV-20A3, Serial NO: SSI-3-0536; LC-20AD Serial NO: L20104551674 USB and L20104551673 USB), CTC Analytics HTC PAL System (Serial NO: 4353);
MS: AB API4000 Q Trap LC/MS/MS instrument (Serial NO. AR19020706)
Column: Phenomenex Luna 5μ C18 (2.0×50 mm)
Mobile phase: 100% acetonitrile (2 mM ammonium acetate) and 100% water (2 mM ammonium acetate)
Quantitative Method: internal standard method Pharmacokinetic curves of compound 1, compound 2 and compound 3 are respectively shown in FIG. 1A, FIG. 1B and FIG. 1C, and the comparative results of the pharmacokinetic data of compound 1, compound 2 and compound 3 are shown in Table 5.

TABLE 5

Comparison of pharmacokinetic data of compound 1, compound 2 and compound 3

| Dose of drug 10 mg/kg | Cl_obs (mL/min/kg) | $t_{1/2}$ (h) | $t_{max}$ (h) | $C_0$ (ng/mL) | $AUC_{last}$ (h*ng/mL) | $AUC_{inf}$ (h*ng/mL) | MRT (h) | Vss_obs (L/kg) | F (%) |
|---|---|---|---|---|---|---|---|---|---|
| Compound 1, administrated intravenously | 2.99 | 3.95 | NA | 10995 | 55767 | 56517 | 4.76 | 0.903 | NA |
| Compound 1, administrated orally | NA | 4.14 | 1.25 | 3880 | 41386 | 39056 | NA | NA | 69.1 |
| Compound 2, administrated intravenously | 1.59 | 9.8 | NA | 11269 | 87835 | 106593 | 7.35 | 1.18 | NA |
| Compound 2, administrated orally | NA | 30.0 | 1.25 | 5090 | 77321 | 192643 | NA | NA | 88 |
| Compound 3, administrated intravenously | 0.75 | 28.3 | NA | 6635 | 112551 | 259986 | 10.1 | 1.56 | NA |
| Compound 3, administrated orally | NA | 20.4 | 8 | 1400 | 20842 | 44697 | NA | NA | 17.2 |

NA: Data was not obtained.

By comparing the pharmacokinetic data of compound 2 and the existing SGLT2 inhibitor compound 1 in Table 5, it is indicated that the clearance rate in vivo of compound 2 is lower than that of compound 1, but its half-life is significantly longer than that of compound 1: in the case of intravenous administration, the half-life of compound 2 is 9.8 hours, which is more than twice the half-life of compound 1; moreover, in terms of oral bioavailability, compound 2 achieves availability of 88%, which is also superior to that of compound 1. Therefore, it can be seen that compound 2 is very stable in the stability test in vivo of SD rats, and significantly superior to the existing SGLT2 inhibitor compound 1.

By comparing the pharmacokinetic data of compound 3 and compound 1 in Table 5, it is indicated that the absorption rate of compound 3 is lower, however, its half-life is longer, which also shows good stability in vivo.

EXAMPLE 5

Pharmacodynamic Test In vivo—Oral Glucose Tolerance Test

In vivo efficacy of compound 2 and compound 3 of the present invention and the known compound 1 were detected in this embodiment.
Method:
Compound 1, compound 2 and compound 3 were respectively dissolved in blank solutions (5% 1-methyl-2-pyrrolidinone, 20% PEG-400 and 20 mM sodium diphosphate) in the concentration of 10 g/L.

Experimental animals are male SD rats of 6-8 weeks old, with weight of 190-215 g, which were purchased from Beijing Vital River Laboratory Animal Technology Co., Ltd. The SD rats were randomly divided into four groups based on body weight, each group containing three rats. Wherein group 1 is the blank control group in which the rats were administrated with the above blank solution. Doses and routes of administration of the rats in each group are shown in Table 6.

TABLE 6

Grouping and administration for oral glucose tolerance test

| Group | Drug | Dose of drug (mg/kg) | Route | Number |
|---|---|---|---|---|
| Group 1 | Blank solution | 0 | Administrated orally | 3 |
| Group 2 | Compound 1 | 10 | Administrated orally | 3 |
| Group 3 | Compound 2 | 10 | Administrated orally | 3 |
| Group 4 | Compound 3 | 10 | Administrated orally | 3 |

Before the test, the rats were fasted for 16 hours and then administrated orally with the blank solution or compounds. The blood glucose baseline level was measured at 15 minutes after administration, then the rats in each group were administrated orally with 50% glucose aqueous solution in an amount of 2 g/kg. The blood samples (1 drop) were taken from tail veins of rats in each group at 15 minutes, 30 minutes, 1 hour and 2 hours after oral administration of glucose, and the blood glucose level was measured by using Accu-Chek Aviva system.

Statistical analysis was conducted and the significance level was set to be $P<0.05$. The mean and standard deviation were calculated for all measurement parameters which were designed for study. One-way analysis of variance (ANOVA) was performed by software GraphPad Prism 5.0 after multiple comparisons among groups.

The blood glucose concentration and $\Delta$AUC were calculated, with results shown in Table 7 and FIG. 2A and FIG. 2B.

It is indicated from the data in Table 7 that, compared with the blank control group (namely group 1), compound 2 and compound 3 of the present invention also have the effect of lowering blood glucose level.

EXAMPLE 6

Pharmacodynamic Tests in vivo—Detection of Blood Glucose and Urine Glucose

Blood glucose and urine glucose levels after oral administration of compound 2 and compound 3 of the present invention and the known compound 1 were detected in this Example, so as to further validate in vivo efficacy of the compounds.

Preparation of the administrated drugs, and grouping and administration of the animals were the same as those in Example 5.

Before the test, the rats were fasted for 16 hours and then administrated orally with the blank solution or compounds. The blood glucose baseline level was measured at 8 hours after administration, then the rats in each group were administrated orally with 50% glucose aqueous solution in an amount of 2 g/kg. The blood samples (1 drop) were taken from tail veins of rats in each group at 15 minutes, 30 minutes, 1 hour and 2 hours after oral administration of glucose, and the blood glucose level was measured by using Accu-Chek Aviva system.

At the end of the test, urine of the rats in each group was collected, and then the urine glucose level was analyzed by using TOSHIBA TBA-40FR automatic biochemical analyzer.

Statistical analysis was conducted and the significance level was set to be $P<0.05$. The mean and standard deviation were calculated for all measurement parameters which were designed for study. One-way analysis of variance (ANOVA) was performed by software GraphPad Prism 5.0 after multiple comparisons among groups.

TABLE 7

Results of oral glucose tolerance test (Mean ± SD)

| Group | Blood glucose (mg/dL) | | | | | $\Delta$AUC (mg/dL*hr) |
|---|---|---|---|---|---|---|
| | 0 | 15 minutes | 30 minutes | 1 hour | 2 hours | |
| Group 1 (Blank solution) | 76.8 ± 1.04 | 168.6 ± 15.52 | 188.4 ± 4.53 | 165.0 ± 5.20 | 106.2 ± 4.76 | 145.7 ± 10.08 |
| Group 2 (Compound 1) | 85.2 ± 4.53 | 97.2 ± 17.36 * | 102.6 ± 20.44 ** | 94.8 ± 17.11 ** | 72.0 ± 10.95 | 20.2 ± 19.32 *** |
| Group 3 (Compound 2) | 85.8 ± 2.75 | 126.6 ± 26.11 | 143.4 ± 24.44 | 138.6 ± 17.17 | 97.2 ± 13.59 | 77.2 ± 20.44 * |
| Group 4 (Compound 3) | 90.0 ± 13.59 | 143.4 ± 18.91 | 172.8 ± 25.01 | 148.2 ± 11.98 | 88.8 ± 17.11 | 87.6 ± 15.90 |

Note:
relative to group 1,
* $p < 0.05$,
** $p < 0.01$,
*** $p < 0.001$ (A) The blood glucose concentration and ΔAUC were calculated, with results shown in Table 8 and FIG. 3.

TABLE 8

Results of oral glucose tolerance test (Mean ± SD)

| Group | Blood glucose (mg/dL) | | | | | ΔAUC |
| --- | --- | --- | --- | --- | --- | --- |
| | 0 | 15 minutes | 30 minutes | 1 hour | 2 hours | (mg/dL*hr) |
| Group 1 (Blank solution) | 92.40 ± 11.98 | 159.60 ± 5.79 | 223.20 ± 6.49 | 188.40 ± 17.67 | 129.00 ± 4.16 | 156.20 ± 19.48 |
| Group 2 (Compound 1) | 50.40 ± 9.52 *** | 96.60 ± 21.70 *** | 131.40 ± 8.25 *** | 123.60 ± 4.53 *** | 72.60 ± 6.81 *** | 107.90 ± 8.53** |
| Group 3 (Compound 2) | 62.40 ± 2.75** | 103.20 ± 12.64** | 154.20 ± 2.75 *** | 141.00 ± 2.08** | 85.20 ± 1.04 *** | 115.00 ± 3.55* |
| Group 4 (Compound 3) | 90.00 ± 1.80 | 148.80 ± 9.06 | 198.60 ± 8.51 | 183.00 ± 12.25 | 128.40 ± 3.75 | 144.40 ± 18.72 |

Note:
relative to group 1,
*p < 0.05,
**p < 0.01,
*** p < 0.001

It is indicated from the data in Table 8 that, in the case of administrating glucose at 8 hours after administration of compound 2 and compound 3 of the present invention, compared with the blank control group (namely group 1), compound 2 and compound 3, particularly compound 2 also has the effect of lowering blood glucose level.

Figure 4:
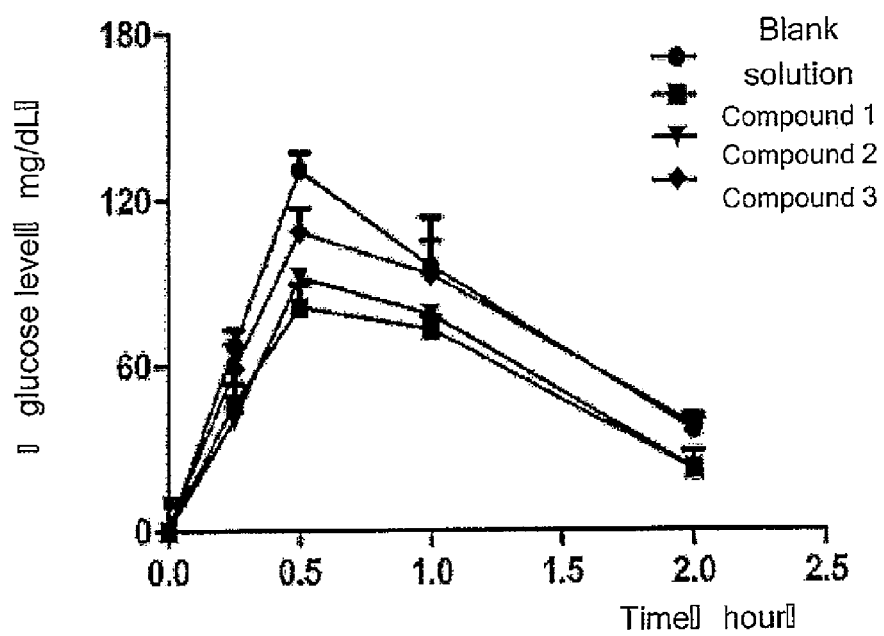
FIG. 4 shows blood glucose test results of the glucose tolerance test in Example 6, wherein 4A represents blood glucose level (mg/mL); 4B represents ΔAUC value of each group (mg/dL*hr), where group 1 is blank solution, group 2 is compound 1, group 3 is compound 2, and group 4 is compound 3.
Figure 4:
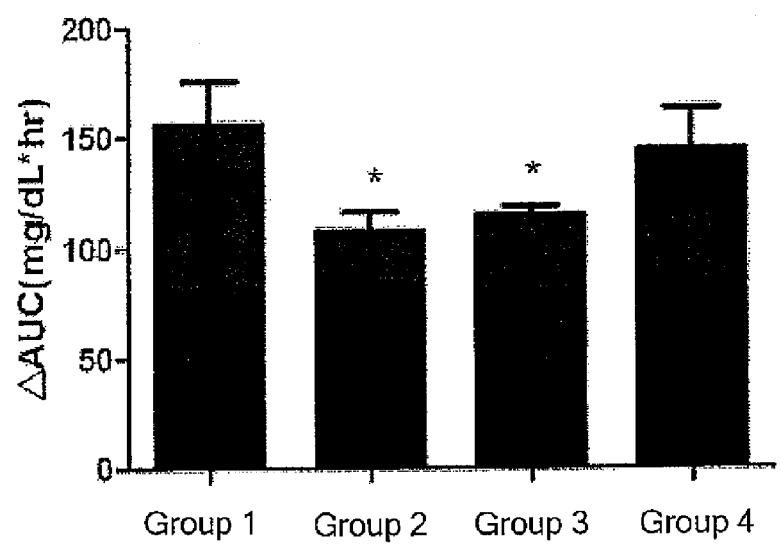

(B) Δglucose level (mg/mL) and ΔAUC (mg/dL*hr) of each group were calculated based on the glucose baseline level, with results shown in FIG. 4A and FIG. 4B. It is indicated from the data that, compared with the blank control group (namely group 1), compound 2 and compound 3, particularly compound 2, also has the effect of lowering blood glucose level. And the effect of compound 2 is close to that of compound 1.

Figure 5:
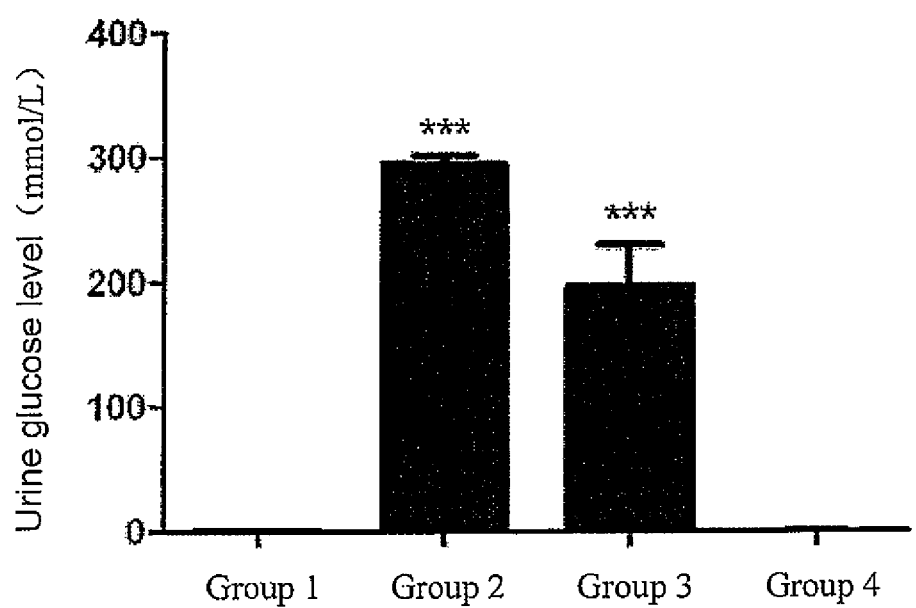
FIG. 5 shows urine glucose test results of the glucose tolerance test in Example 6.

(C) Analysis results of urine glucose are shown in Table 9 and FIG. 5.

TABLE 9

Analysis results of urine glucose (Mean ± SD)

| Group | Urine glucose (mmol/L) |
| --- | --- |
| Group 1 (blank solution) | 0.40 ± 0.25 |
| Group 2 (compound 1) | 294.90 ± 12.29*** |
| Group 3 (compound 2) | 197.90 ± 56.27*** |
| Group 4 (compound 3) | 0.10 ± 0.17 |

Note:
relative to the blank control group, ***p < 0.001

It is known in the art that, there is no glucose in urine. This is because blood is filtrated through glomerulus and all of blood glucose filtrated enters into the crude urine and then reabsorbed after passing through renal proximal tubule. This reabsorption procedure is performed through sodium-glucose co-transport protein (SGLTs), and one of SGLTs (that is SGLT2) is responsible for reabsorption of over 90% of the glucose. It is known from analysis results of blood glucose and urine glucose that, compared to the blank control group, the urine glucose level of the rat after oral administration of compound 2 of the present invention was significantly increased, and the effect of compound 2 is close to that of the existing known SGLT2 inhibitor compound 1, which indicates that compound 2 of the present invention is also able to inhibit SGLT2, thereby reducing blood glucose.

In conclusion, the experiments prove that compound 2 of the present invention can inhibit renal reabsorption of urine glucose and decrease blood glucose, and its efficacy is equal to or better than that of the existing drug dapagliflozin (compound 1) for treating type II diabetes. Meanwhile, compared to compound 1, compound 2 of the present invention has longer half-life in vivo and higher oral absorption rate, making it more suitable to be prepared in a variety of dosage forms, thus facilitating to the administration of drugs. Therefore, compound 2 of the present invention is a potential drug with superior effect, which can be used for treating diseases related to SGLT2, especially diabetes and related diseases.

Formulation examples of the pharmaceutical composition of the present invention are provided hereinafter, wherein "active ingredient" in each example represents the compound or the pharmaceutically acceptable salt, solvate, polymorph, enantiomer or racemic mixture thereof provided by the present invention.

EXAMPLE 7

Tablet

A single tablet contains the following ingredients:

| | |
| --- | --- |
| active substance | 10 mg |
| lactose | 100 mg |
| corn starch | 40 mg |
| polyvinylpyrrolidone | 5 mg |
| magnesium stearate | 2 mg |

Preparation Method:
The mixture of lactose and corn starch was wetted with 20% polyvinylpyrrolidone aqueous solution, and then sieved by a sieve with 1.5 mm sieve pore. The granules were dried at 45° C., sieved again and then mixed with magnesium stearate for tabletting.

EXAMPLE 8

Capsule

A single capsule contains the following ingredients:

| | |
| --- | --- |
| active substance | 10 mg |
| lactose | 100 mg |
| corn starch | 40 mg |

| | |
|---|---|
| polyvinylpyrrolidone | 5 mg |
| magnesium stearate | 2 mg |

Preparation Method:

The mixture of lactose and corn starch was wetted with 20% polyvinylpyrrolidone aqueous solution, and then sieved by a sieve with 1.5 mm sieve pore. The granules were dried at 45° C., sieved again and then filled into hard capsule.

EXAMPLE 9

Infection

A 2 ml ampoule contains the following ingredients:

| | |
|---|---|
| active substance | 10 mg |
| 0.01 N hydrochloric acid | q.s. |
| NaCl | q.s. |
| double-distilled water | q.s. |

Preparation Method:

The active substance was dissolved in an appropriate amount of 0.01 N HCl, NaCl was added into the mixture to make it isotonic, and water was added into the mixture such that the volume of the mixture reach 2 ml, then the mixture was sterilized and transferred to an ampoule to gain injection.

What is claimed is:

1. A compound of formula I or a pharmaceutically acceptable salt, solvate, polymorph, enantiomer or racemic mixture thereof,

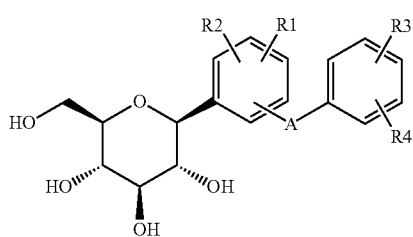

wherein R1 and R2 are each independently hydrogen, —OH, alkyl, —CF$_3$, —OCHF$_2$, —OCF$_3$ or halogen;

R3 is —OCH$_2$CF$_3$, —OCH$_2$CHF$_2$, —OCH$_2$CH$_2$F or —OCH$_2$CH$_3$;

R4 is hydrogen, —OH, —O aryl, —OCH$_2$ aryl, alkyl, cycloalkyl, —CF$_3$, —OCHF$_2$, —OCF$_3$, —OCH$_2$CF$_3$, —OCH$_2$CHF$_2$, —OCH$_2$CH$_2$F or halogen;

A is —CX$_1$X$_2$, wherein X$_1$ and X$_2$ are each independently H and Cl, and when both X1 and X2 are H, R3 is not —OCH$_2$CH$_3$.

2. The compound or the pharmaceutically acceptable salt, solvate, polymorph, enantiomer or racemic mixture thereof according to claim 1, wherein the compound is as shown in formula Ia:

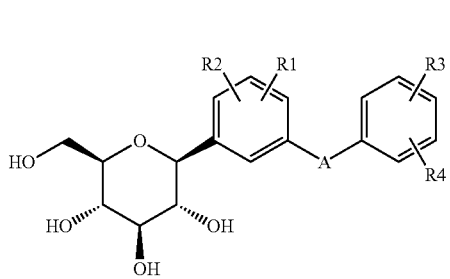

wherein R1 to R4 and A are defined as in claim 1.

3. The compound or the pharmaceutically acceptable salt, solvate, polymorph, enantiomer or racemic mixture thereof according to claim 1, wherein the compound is as shown in formula Ib:

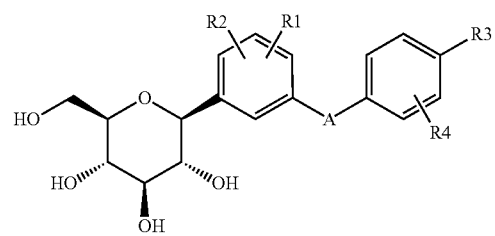

wherein R1 to R4 and A are defined as in claim 1.

4. The compound or the pharmaceutically acceptable salt, solvate, polymorph, enantiomer or racemic mixture thereof according to claim 1, wherein the compound is as shown in formula Ic:

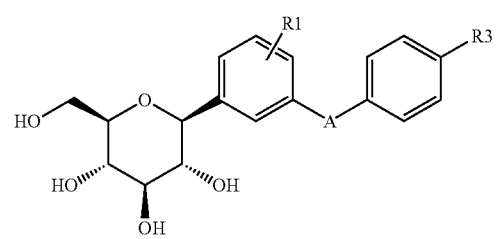

wherein R1, R3 and A are defined as in claim 1.

5. The compound or the pharmaceutically acceptable salt, solvate, polymorph, enantiomer or racemic mixture thereof according to claim 1, wherein the compound is as shown in formula Id:

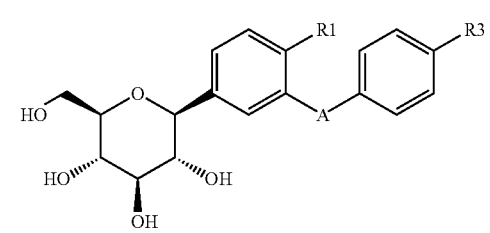

wherein R1, R3 and A are defined as in claim 1.

6. The compound or the pharmaceutically acceptable salt, solvate, polymorph, enantiomer or racemic mixture thereof according to claim 1, wherein R3 is —OCH$_2$CF$_3$, —OCH$_2$CHF$_2$ or —OCH$_2$CH$_2$F.

7. The compound or the pharmaceutically acceptable salt, solvate, polymorph, enantiomer or racemic mixture thereof according to claim 1, wherein R3 is —OCH$_2$CF$_3$.

8. The compound or the pharmaceutically acceptable salt, solvate, polymorph, enantiomer or racemic mixture thereof according to claim 1, wherein both X$_1$ and X$_2$ are hydrogen.

9. The compound or the pharmaceutically acceptable salt, solvate, polymorph, enantiomer or racemic mixture thereof according to claim 1, wherein R1 is halogen.

10. The compound or the pharmaceutically acceptable salt, solvate, polymorph, enantiomer or racemic mixture thereof according to claim 9, wherein R1 is Cl.

11. The compound or the pharmaceutically acceptable salt, solvate, polymorph, enantiomer or racemic mixture thereof according to claim 1, wherein R2 is hydrogen.

12. The compound or the pharmaceutically acceptable salt, solvate, polymorph, enantiomer or racemic mixture thereof according to claim 1, wherein R4 is hydrogen.

13. The compound or the pharmaceutically acceptable salt, solvate, polymorph, enantiomer or racemic mixture thereof according to claim 1, wherein the structure of the compound is shown as follows:

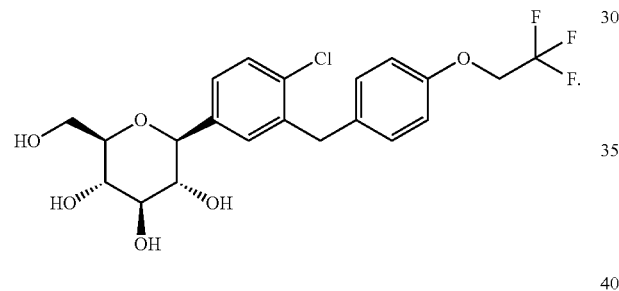

14. A method for preparing the compound or the pharmaceutically acceptable salt, solvate, polymorph, enantiomer or racemic mixture thereof according to claim 1, comprising the step of reacting a compound of formula IX with a compound of formula X,

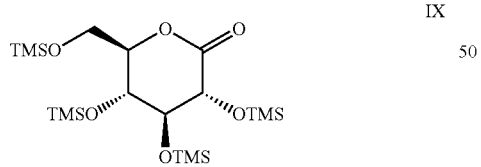

IX

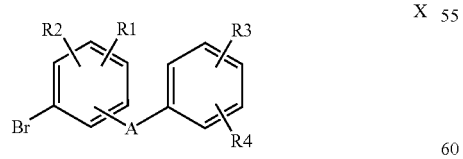

X wherein R1 to R4 and A are defined as in claim 1.

15. The method according to claim 14, wherein the method comprises the following steps:

(1) reacting a compound of formula III with Trimethylsilyl chloride to generate the compound of formula IX:

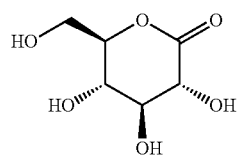

III (2) reacting a compound of formula IV with (COCl)$_2$ to generate a compound of formula V:

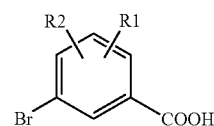

IV

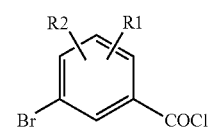

V (3) reacting the compound of formula V with a compound of formula VI in the presence of AlCl$_3$ to generate a compound of formula VII:

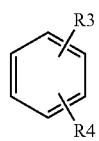

VI

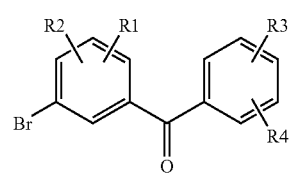

VII (4) reducing the carbonyl group in the compound of formula VII and/or reacting the carbonyl group to form a halogenated alkyl group to produce the compound of formula X;

(5) reacting the compound of formula IX with the compound of formula X in the presence of n-butyl lithium, methanol and methanesulfonic acid to produce a compound of formula XI:

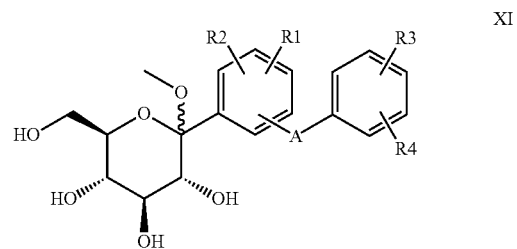

XI and
(6) converting the compound of formula XI into the compound of formula I in the presence of $Et_3SiH$ and $BF_3.Et_2O$;
wherein R1 to R4 and A are defined as in claim 1.

16. The method according to claim 15, wherein in step (1), the compound of formula III is reacted with Trimethylsilyl chloride in the presence of N-methylmorpholine.

17. The method according to claim 15, wherein step (4) comprises:
reducing the carbonyl group fully in the presence of $Et_3SiH$ and $BF_3.Et_2O$; or step (4) comprises: reacting the carbonyl group in the presence of ethane-1,2-dithiol and $BF_3.2HOAc$ to form dithiolane and then causing the dithiolane to form a halogenated alkyl group by a select-halogen reagent.

18. A pharmaceutical composition comprising the compound or the pharmaceutically acceptable salt, solvate, polymorph, enantiomer or racemic mixture thereof according to claim 1, and a pharmaceutically acceptable excipient.

19. The pharmaceutical composition according to claim 18, wherein the pharmaceutical composition is a tablet, suppository, dispersible tablet, enteric-coated tablet, chewable tablet, orally disintegrating tablet, capsule, sugar-coated agent, granule, dry powder, oral solution, small needle for injection, lyophilized powder or large volume parenteral for injection.

20. The pharmaceutical composition according to claim 18, wherein the pharmaceutically acceptable excipient comprises one or more of the following excipients: diluents, solubilizers, disintegrating agents, suspending agents, lubricants, binders, fillers, flavoring agents, sweeteners, antioxidants, surfactants, preservatives, wrapping agents and pigments.

21. The pharmaceutical composition according to claim 18, wherein the pharmaceutical composition further comprises one or more medicaments selected from: anti-diabetic agents, anti-obesity agents, anti-hypertensive agents, anti-atherosclerotic agents and lipid-lowering agents.

22. The pharmaceutical composition according to claim 21, wherein the pharmaceutical composition further comprises an anti-diabetic agent.

23. A method for treating or delaying the following diseases: diabetes, hyperglycemia, hyperinsulinemia, hyperlipidemia, obesity, X syndrome, hypertriglyceridemia, atherosclerosis, hypertension or diabetic complication, the method comprising: administering to a patient in need thereof a therapeutically effective amount of the compound or the pharmaceutically acceptable salt, solvate, polymorph, enantiomer or racemic mixture thereof according to claim 1.

\* \* \* \* \*